US009522026B2

(12) United States Patent
Songer

(10) Patent No.: US 9,522,026 B2
(45) Date of Patent: Dec. 20, 2016

(54) CABLE SYSTEM FOR SURGICAL APPLICATION

(76) Inventor: Matthew N. Songer, Marquette, MI (US)

( * ) Notice: Subject to any disclaimer, the term of this patent is extended or adjusted under 35 U.S.C. 154(b) by 896 days.

(21) Appl. No.: 13/397,804

(22) Filed: Feb. 16, 2012

(65) Prior Publication Data
US 2012/0215224 A1 Aug. 23, 2012

Related U.S. Application Data

(60) Provisional application No. 61/443,766, filed on Feb. 17, 2011.

(51) Int. Cl.
A61B 17/56 (2006.01)
A61B 17/58 (2006.01)
A61B 17/82 (2006.01)
A61B 17/84 (2006.01)

(52) U.S. Cl.
CPC ............. *A61B 17/82* (2013.01); *A61B 17/842* (2013.01)

(58) Field of Classification Search
CPC ...... A61B 17/82; A61B 17/823; A61B 17/826
USPC .......................................... 606/74, 151, 263
See application file for complete search history.

(56) References Cited

U.S. PATENT DOCUMENTS

| 4,966,600 | A | 10/1990 | Songer et al. |
|---|---|---|---|
| 5,116,340 | A | 5/1992 | Songer et al. |
| 5,415,658 | A | 5/1995 | Kilpela et al. |
| 5,536,270 | A | 7/1996 | Songer et al. |
| 5,611,801 | A | 3/1997 | Songer |
| 5,649,927 | A | 7/1997 | Kilpela et al. |
| 5,693,046 | A | 12/1997 | Songer et al. |
| 5,702,399 | A | 12/1997 | Kilpela et al. |
| 5,741,260 | A | 4/1998 | Songer et al. |
| 5,788,697 | A | 8/1998 | Kilpela et al. |
| 5,935,130 | A | 8/1999 | Kilpela et al. |
| 5,964,769 | A | 10/1999 | Wagner et al. |
| 6,086,590 | A | 7/2000 | Margulies et al. |
| 6,364,885 | B1 | 4/2002 | Kilpela et al. |
| 6,595,994 | B2 | 7/2003 | Kilpela et al. |
| 6,730,092 | B2 | 5/2004 | Songer |
| 7,090,675 | B2 | 8/2006 | Songer |
| 7,207,090 | B2 | 4/2007 | Mattchen |
| 7,255,701 | B2 | 8/2007 | Allen et al. |
| 8,241,288 | B2 | 8/2012 | Justin et al. |
| 2008/0208223 | A1* | 8/2008 | Kraemer ................ 606/151 |
| 2010/0249845 | A1* | 9/2010 | Meunier et al. ........ 606/263 |
| 2010/0256612 | A1* | 10/2010 | Dell'Oca ................ 606/1 |

* cited by examiner

Primary Examiner — Matthew Lawson
(74) Attorney, Agent, or Firm — Wood, Phillips, Katz, Clark & Mortimer

(57) ABSTRACT

A surgical cable system having a length of cable and a locking body on which a first cable end is operatively located. The locking body defines a receiver for a first portion of the cable with the cable formed into a first loop that resides generally in a first plane. A locking structure on the locking body cooperates with the first portion of the cable to maintain the first loop in a tensioned state. The locking structure has an actuator that is operable to change the state of the locking structure. The locking structure is changeable from a released state into a locked state as an incident of one of: a) moving at least a part of the actuator along and/or around an axis that is generally parallel to the first plane; and b) moving a part of the cable length along a first line that is generally parallel to the first plane.

21 Claims, 15 Drawing Sheets

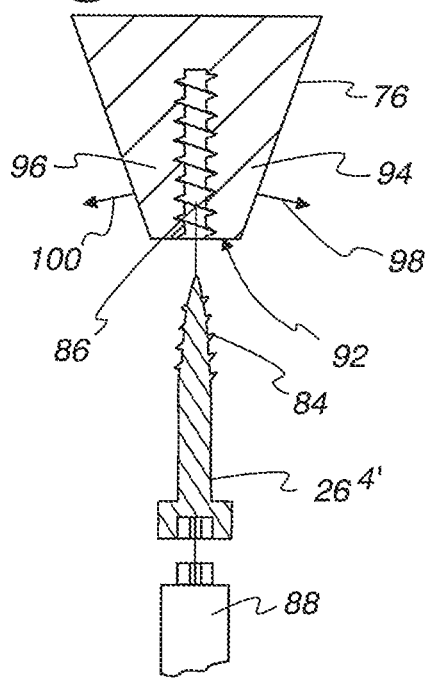
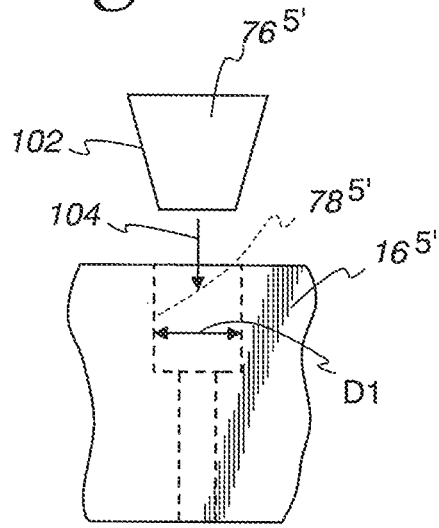
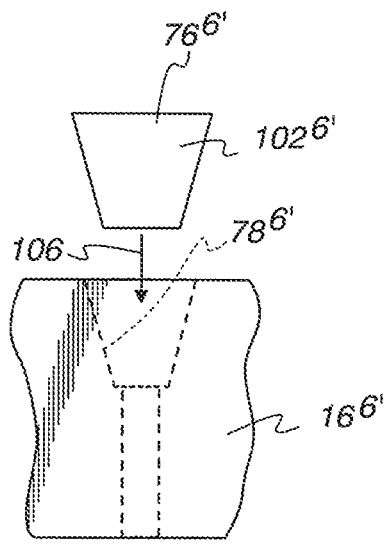
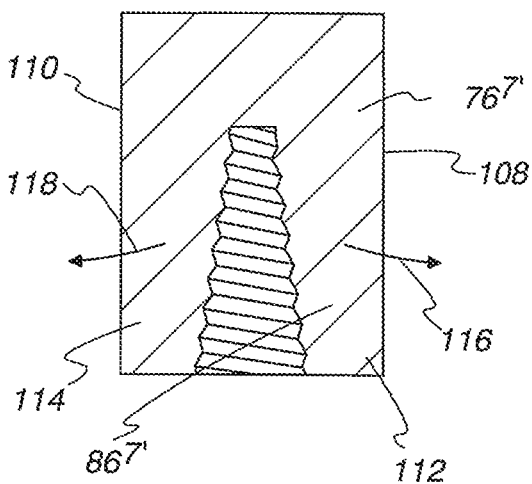

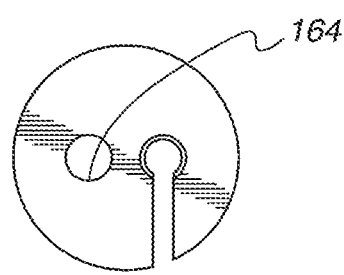
Fig. 29
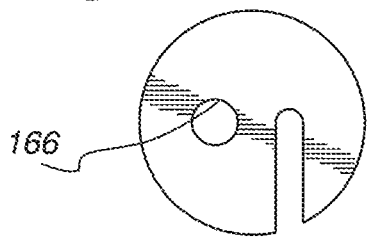
Fig. 30
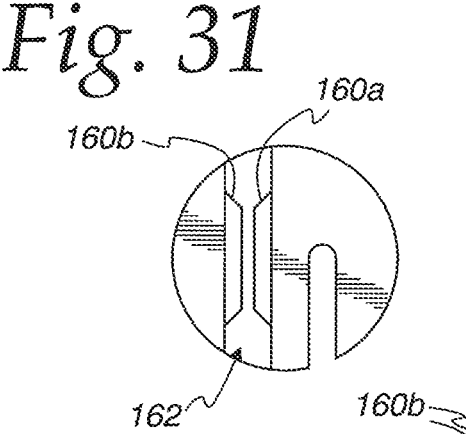
Fig. 31
Fig. 32
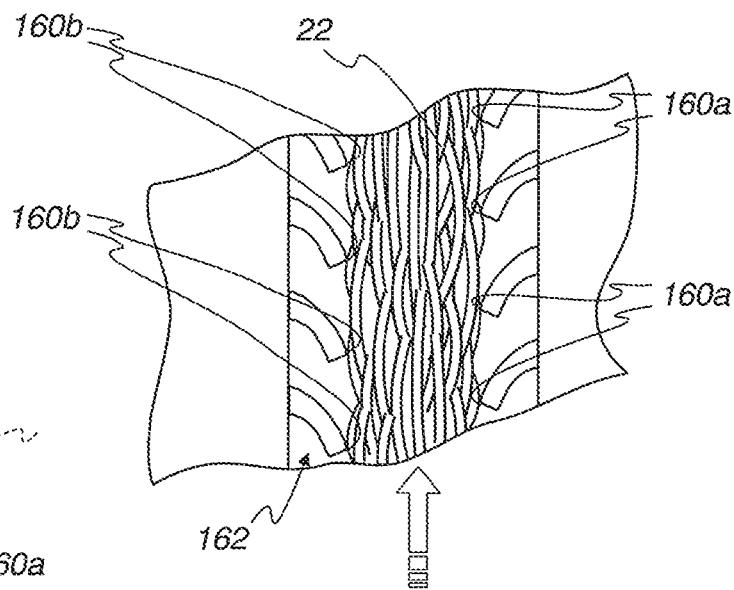
Fig. 33
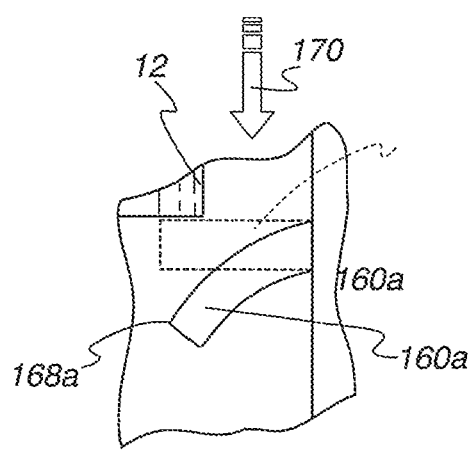

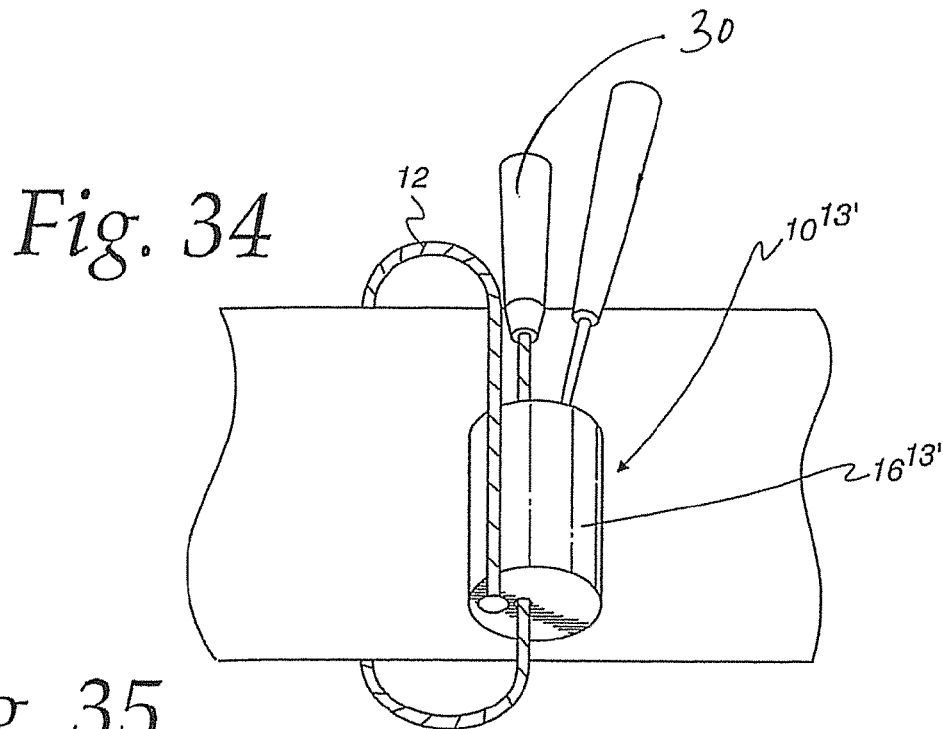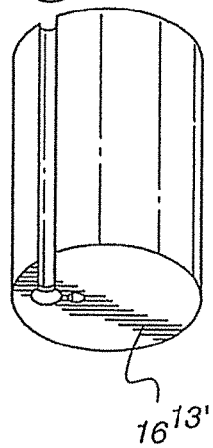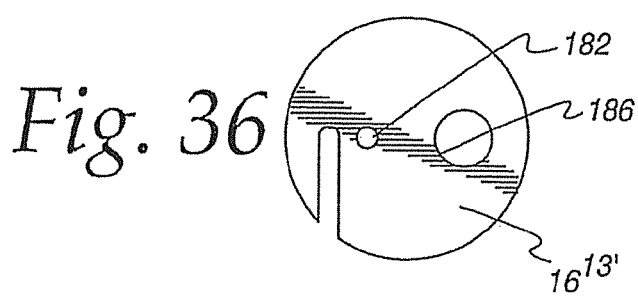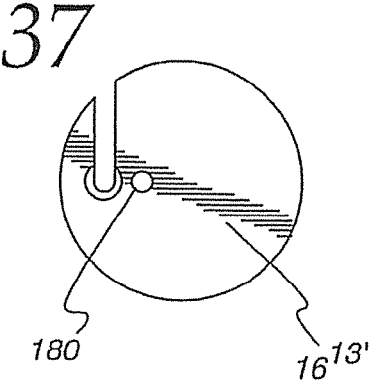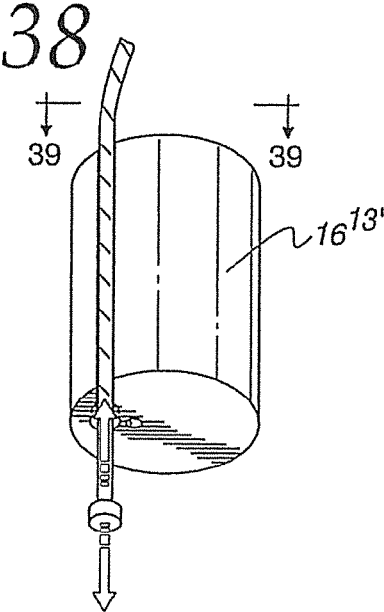

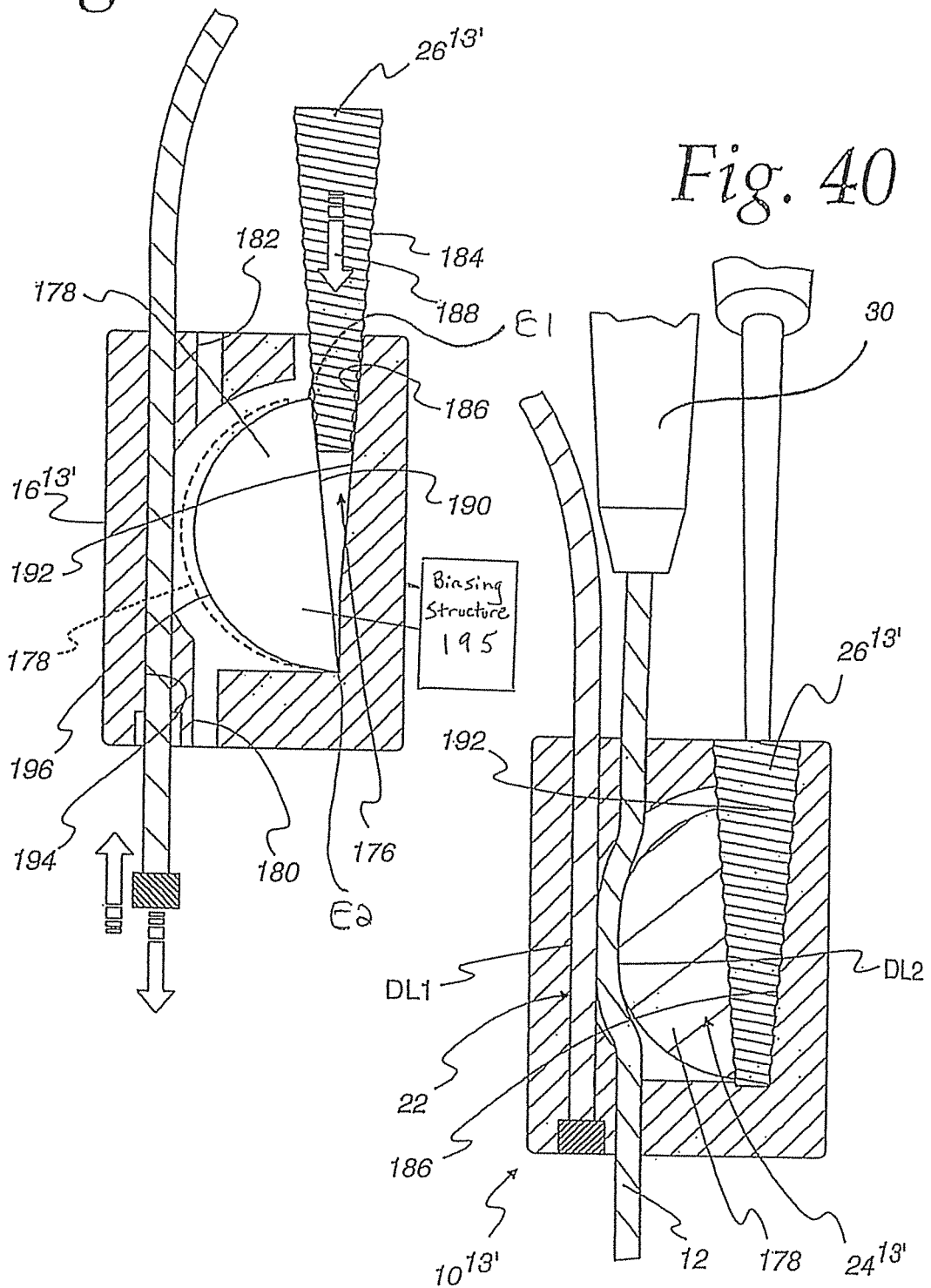

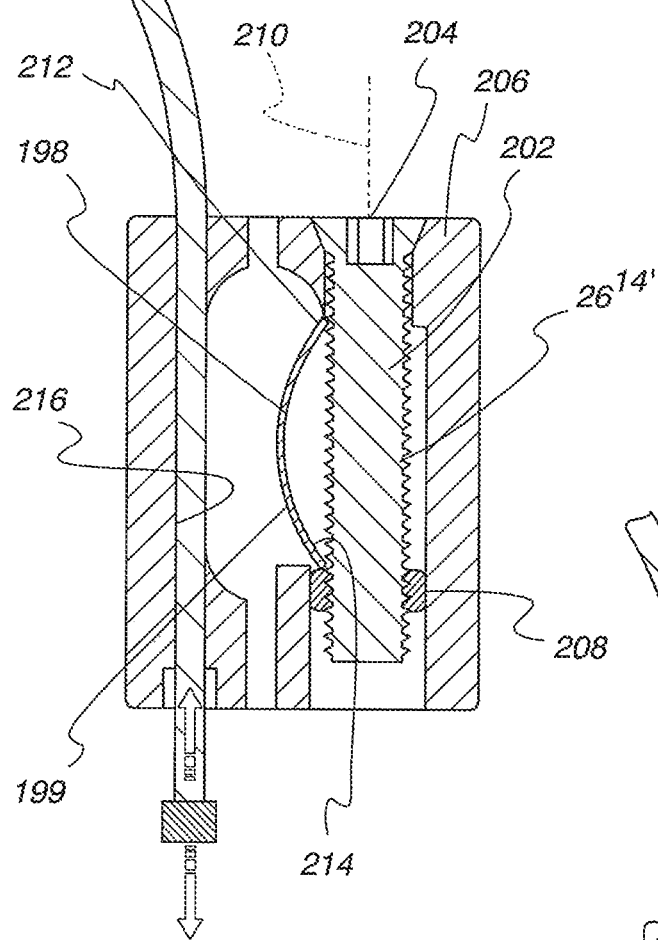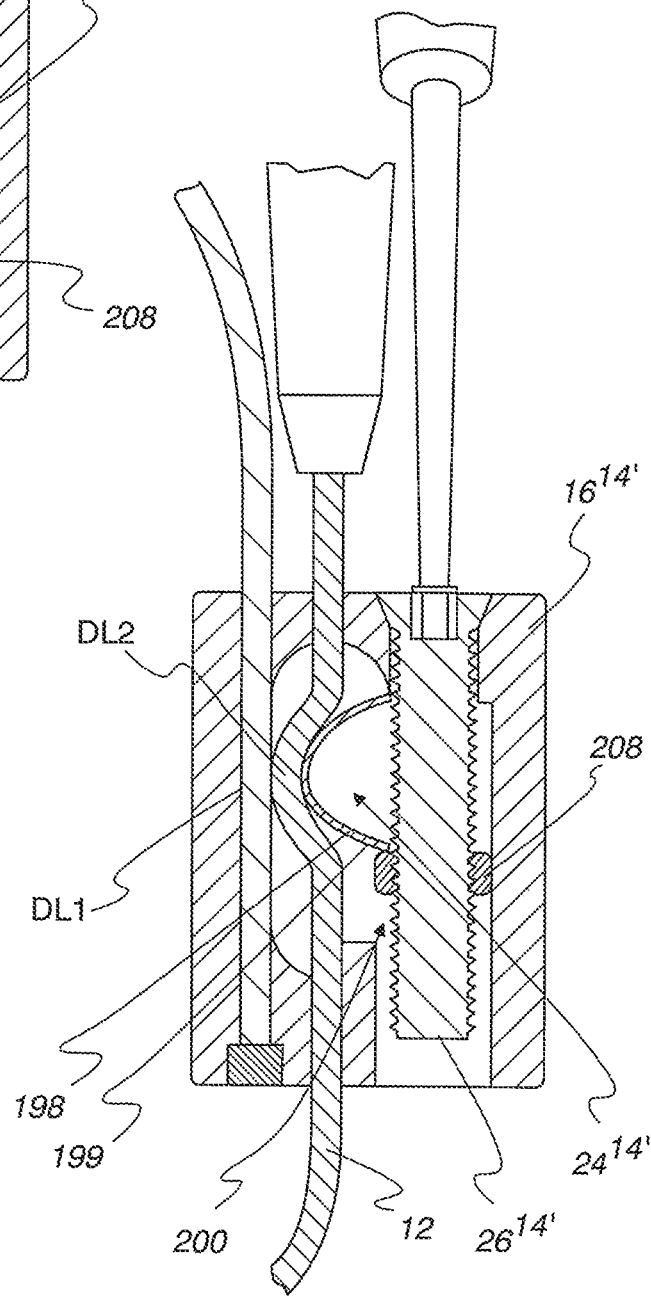

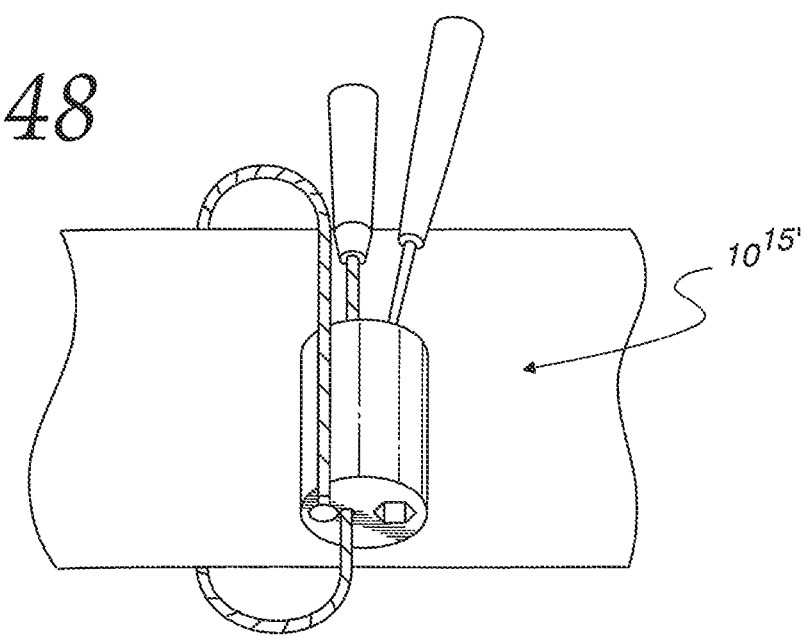
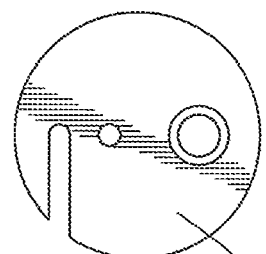
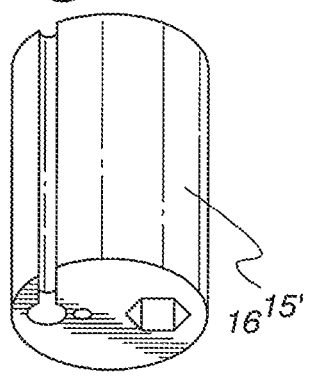
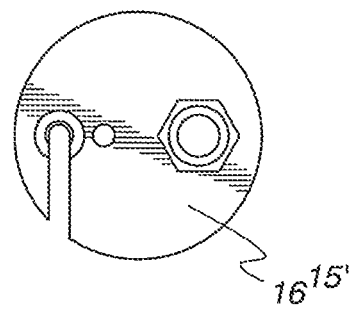
Fig. 48
Fig. 49
Fig. 50
Fig. 51
Fig. 52

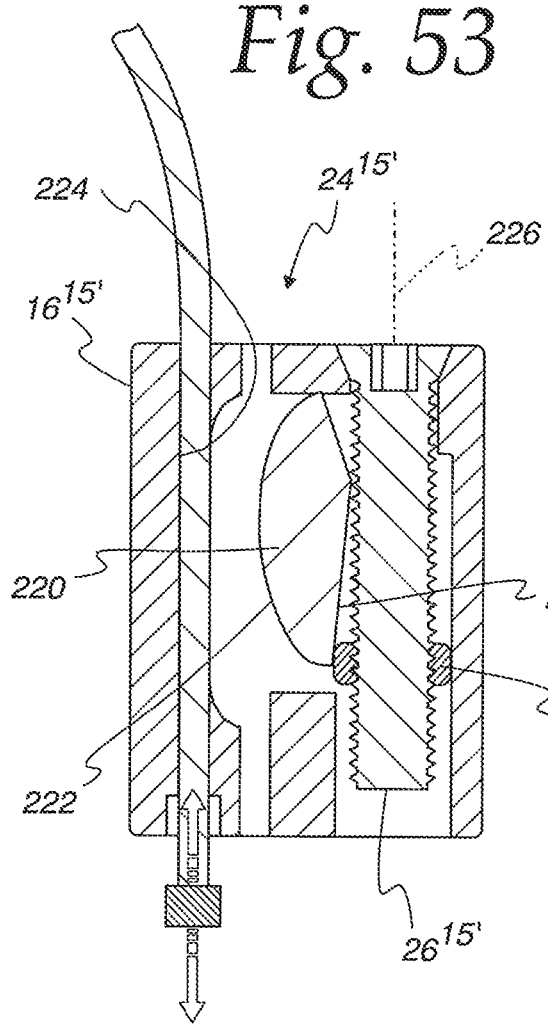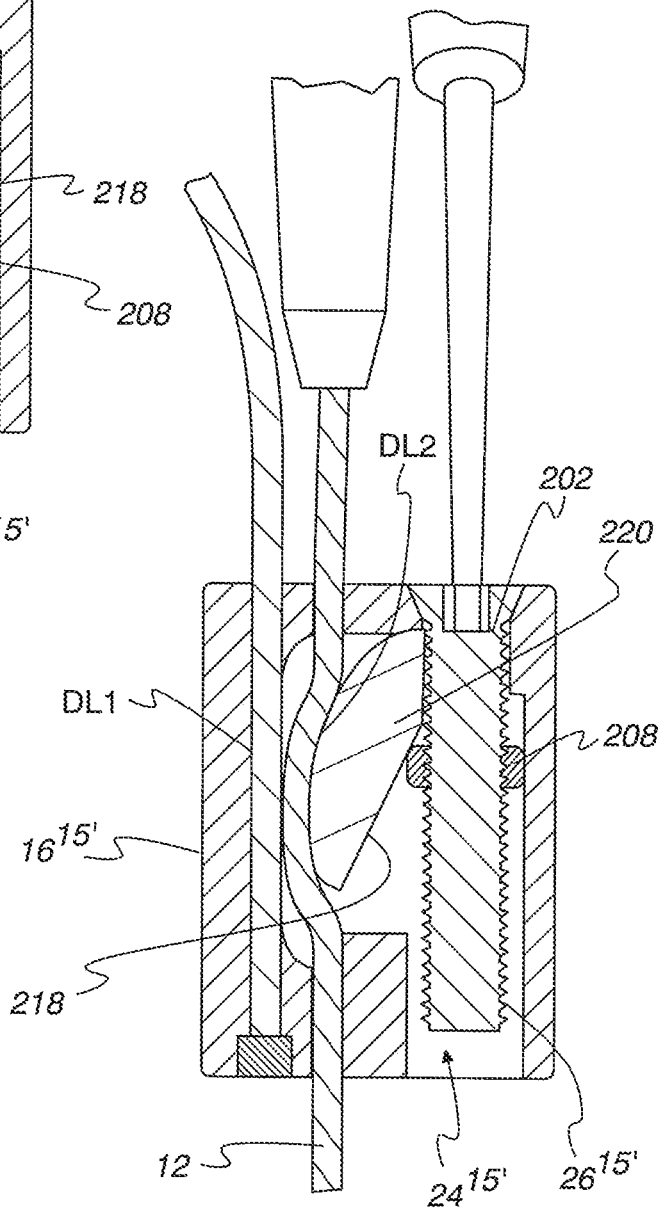

CABLE SYSTEM FOR SURGICAL APPLICATION

CROSS-REFERENCE TO RELATED APPLICATIONS

This application is a non-provisional of U.S. Ser. No. 61/443,766, filed Feb. 17, 2011.

BACKGROUND OF THE INVENTION

Field of the Invention

This invention relates to cable systems used to perform different surgical procedures and, more particularly, to a system for fixing a cable in a tensioned state relative to a bone or bone fragment that is to be maintained in a desired relationship to another bone, an implant, and/or a bone fragment by the cable.

Background Art

A multitude of cable systems for surgical applications have been developed over the past several decades. The inventor herein, by himself and in conjunction with others, made a number of developments in this area over the time period between the mid-1980's and the present, many of which are the subject of U.S. patents. Among these patents are the following:

| Pat. No. | Issue Date |
|---|---|
| 7,090,675 | Aug. 15, 2006 |
| 6,730,092 | May 4, 2004 |
| 6,595,994 | Jul. 22, 2003 |
| 6,364,885 | Apr. 2, 2002 |
| 6,086,590 | Jul. 11, 2000 |
| 5,935,130 | Aug. 10, 1999 |
| 5,788,697 | Aug. 4, 1998 |
| 5,741,260 | Apr. 21, 1998 |
| 5,702,399 | Dec. 30, 1997 |
| 5,693,046 | Dec. 2, 1997 |
| 5,649,927 | Jul. 22, 1997 |
| 5,611,801 | Mar. 18, 1997 |
| 5,536,270 | Jul. 16, 1996 |
| 5,415,658 | May 16, 1995 |
| 5,116,340 | May 26, 1992 |
| 4,966,600 | Oct. 30, 1990 |

The disclosure in each of these patents is incorporated by reference herein.

Cable system technology is used in performing a wide range of surgical procedures involving bone stabilization, implant stabilization, stabilization of fractured bone segments, etc.

In most of these applications, a cable length is required to be tensioned against or around components that are to be stabilized, each relative to the other, through the cable.

In the early 1980's, cable lengths were maintained in a tensioned state using basic crimp technology. That is, ends of a cable in a loop shape, extending in opposite directions, were held by a simple crimp connector that was squeezed against the surrounded cable ends.

The inventor herein developed an early system that was made from cable with a formed loop. A top hat crimp was threaded on the loose cable end after it had passed around the object, to be fixated, and through the loop. This created a lasso/noose that was tensioned, after which the top hat was crimped to maintain the cable configuration.

The next generation of cable system devised by the inventor herein, in conjunction with others, was one utilizing a crimp body at one cable end in place of the aforementioned loop that allowed the free end of the cable to be directed therethrough. The one end of the cable was swaged and threaded into a cylindrical crimp body until it locked in place. The free cable end was passed around the bone and then through the crimp body. The portion of the cable passing through the body was locked by threading a set screw into the body in a direction perpendicular to the cable length. The set screw squeezed on a crimp component on the cable to hold it in place.

The advantage of this latter system was that only a screwdriver was needed to lock the cable in place. This avoided the need for large crimpers that had to be maneuvered, generally quite awkwardly, to effect a crimp. This configuration also allowed access to difficult locations and offered a less invasive way to tension and crimp a cable.

The primary drawback with this latter system was that the set screw was oriented at 90° to the cable length. As a result, a sizable incision was required and the procedure often necessitated triangulation of a cable tensioner and a screwdriver.

The existing cable systems known to the inventor herein each has limitations that create problems or make procedures more difficult in the surgical environment. Some of these limitations are described below.

Typically, the cables will be drawn in tension using tools configured so that the tool and cable remain substantially in one plane. Crimping of the cable or fixation in any other manner is usually carried out at 90° to the plane of the cable that is normally in a loop form. This cable "locking" structure is usually reconfigured through a large, bulky, and often awkwardly operated crimper.

As described above, even with the inventor's own system, the described set screw requires the use of a screwdriver that is also operated in a direction that is generally orthogonal to the plane of the cable loop.

Another problem with early cable system tensioners is that they were often configured to pull cable from both ends. As a result, the tensioners often required a significant amount of space in which to operate.

Newer tensioning systems operate with a unidirectional capability. However, with these systems, the direction of pulling must be planned and determined ahead of time, requiring that the cable be inserted in a way that is consistent with the pulling direction. The surgeon cannot change his/her mind once the cable is passed, in which event the cable must be redirected and re-passed in the opposite direction.

A further problem with existing cable systems is that they commonly incorporate a permanently fixed component. Once a component is crimped, it cannot be released or otherwise reconfigured to allow readjustment of the cable. The only option to the surgeon is to cut the cable or components thereon to allow loosening, reapplication, or re-tensioning of the same.

SUMMARY OF THE INVENTION

In one form, the invention is directed to a surgical cable system including: a length of cable having a first end; a locking body for the length of cable on which the first cable end is operatively located, the locking body having a receiver for a first portion of the length of cable with the length of cable formed into a first loop that resides generally in a first plane; and a locking structure on the locking body that cooperates with the first portion of the cable so as to maintain the first loop in a tensioned state. The locking structure has a locked state and a released state. The locking structure has an actuator that is operable to change the locking structure from the released state into the locked state in which the tensioned state of the first loop is maintained. The locking structure is changeable from the released state into the locked state as an incident of one of: a) moving at least a part of the actuator along and/or around an axis that is generally parallel to the first plane; and b) moving a part of the cable length along a first line that is generally parallel to the first plane.

In one form, the actuator has a movable tine with an edge that engages a part of the cable length to allow the part of the cable length to move in only one direction as the part of the cable length is moved along a first line that is parallel to the first plane to thereby change the locking structure from the released state into the locked state.

In one form, the tine is cantilever mounted so that the tine edge is biased against the part of the cable length.

In one form, the locking structure is changeable from the released state into the locked state by moving at least a part of the actuator along and/or around an axis that is generally parallel to the first plane.

In one form, the locking structure is operable to change the locking structure from the locked state into the released state to thereby allow tension on the first loop to be reduced and the first loop to be reconfigured.

In one form, the actuator is configured to be operated by a tool that is directed from a separated position into an operative position relative to the part of the actuator by movement of the tool in a plane that is substantially parallel to the first plane.

In one form, the actuator has a threaded portion that is turned around an axis to change the locking structure from the released state into the locked state.

In one form, the locking body is deformed by the actuator as the threaded portion is turned to thereby change the locking structure from the released state into the locked state.

In one form, the actuator is in the form of a wedging component that is turned around an axis to change the locking structure from the released state into the locked state.

In one form, the locking structure has a wedging component that is movable relative to the locking body to change the locking structure from the released state into the locked state.

In one form, the wedging component is separable from the locking body.

In one form, the actuator has a threaded portion that threadably engages the wedging component and moves the wedging component relative to the locking body as the threaded portion is turned around an axis to thereby change the locking structure from the released state into the locked state.

In one form, the actuator has a guide groove and is movable around an axis to change the locking structure from the released state into the locked state. The locking structure further includes a wedging component, the wedging component moving guidingly in the guide groove as the actuator is moved around the axis to change the state of the locking structure.

In one form, the locking structure has a wedging component in the form of a spring element that is reconfigured as the part of the actuator is moved.

In one form, the spring element is a leaf spring and the actuator is threadably engaged with the leaf spring.

In one form, with the locking structure in the locked state a first part of the locking body urges the first portion of the length of cable against a second part of the body.

In one form, the locking structure has a wedging component. With the locking structure in the locked state, a part of the wedging component urges the first portion of the length of cable against the locking body.

In one form, with the locking structure in the locked state the locking body urges one discrete length of the first portion of the length of cable against a second discrete length of the first portion of the length of cable.

In one form, with the locking structure in the locked state the wedging component urges one discrete length of the first portion of the length of cable against a second discrete length of the first portion of the length of cable and against the locking body.

In one form, an anchoring element is provided on the first end of the length of cable and the body defines a seat for the anchoring element in which the anchoring element is blocked.

In one form, the seat is bounded by a shoulder to which the anchoring element abuts and against which the anchoring element can be drawn to produce tension on the length of cable.

In one form, the anchoring element can be releasably pressed into the seat to allow the length of cable to be separated from the locking body.

BRIEF DESCRIPTION OF THE DRAWINGS

FIG. 13 is an enlarged, exploded view of the wedging component in FIG. 12 and an actuator therefor in the form of a threaded screw/bolt;

FIG. 14 is a fragmentary view of a modified form of wedging component and cooperating locking body;

FIG. 15 is a view as in FIG. 14 of a further modified form of wedging component and locking body;

FIG. 16 is a view as in FIG. 13 of a further modified form of locking body;

FIG. 29 is a view of the locking body from one end thereof;

FIG. 30 is a view of the locking body from the end thereof opposite that shown in FIG. 29;

FIG. 31 is a cross-sectional view of the locking body taken along line 31-31 of FIG. 28;

FIG. 32 is an enlarged, fragmentary, elevation view showing tines on the locking assembly cooperating with a cable;

FIG. 33 is an enlarged, fragmentary view of an end of the cable as it approaches one of the tines of FIG. 32 as the cable is advanced into the locking body;

FIG. 34 is a view as in FIG. 26 of a further modified form of locking system, according to the invention, and including a locking body and locking system on the locking body;

FIG. 35 is a perspective view of the locking body in FIG. 34;

FIG. 36 is a view of the locking body from one end thereof;

FIG. 37 is a view of the locking body from the end opposite that in FIG. 36;

FIG. 38 is a perspective view of the cable system and showing an end of a cable separated therefrom;

FIG. 39 is a cross-sectional view of the locking system taken along line 39-39 of FIG. 38 and showing the locking system in a released state;

FIG. 40 is a view as in FIG. 39 with the locking system in a locked state;

FIG. 46 is a cross-sectional view of the cable system taken along line 46-46 of FIG. 45 and showing the locking system in a released state;

FIG. 47 is a view as in FIG. 46 wherein the locking system is in a locked state;

FIG. 48 is a view as in FIG. 41 of a still further modified form of cable system, according to the invention, and including a locking body and locking system;

FIG. 49 is a perspective view of the locking body in FIG. 48;

FIG. 50 is a view of the locking body taken from one end thereof;

FIG. 51 is a view of the body taken from the end opposite that in FIG. 50;

FIG. 52 is a perspective view of the cable system with one end of the cable separated from the locking body;

FIG. 53 is a cross-sectional view of the cable system taken along line 53-53 of FIG. 52 with the locking system in a released state; and FIG. 54 is a view as in FIG. 53 with the locking system in a locked state.

DETAILED DESCRIPTION OF THE PREFERRED EMBODIMENT

Figure 1:
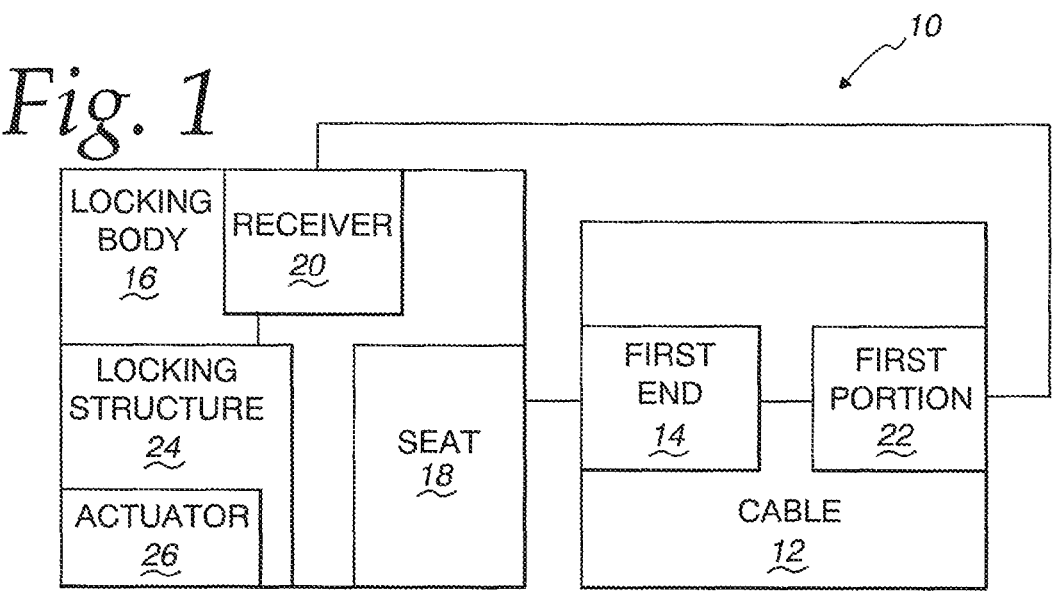
FIG. 1 is a schematic representation of a cable system, according to the invention, used to maintain a cable in a tensioned loop form.

In FIG. 1, a schematic representation of a cable system for surgical applications, according to the invention, is shown at 10. The cable system 10 consists of a length of cable 12 with a first end 14. A locking body 16 has a seat 18 in which the first cable end 14 is operatively located.

Figure 2:
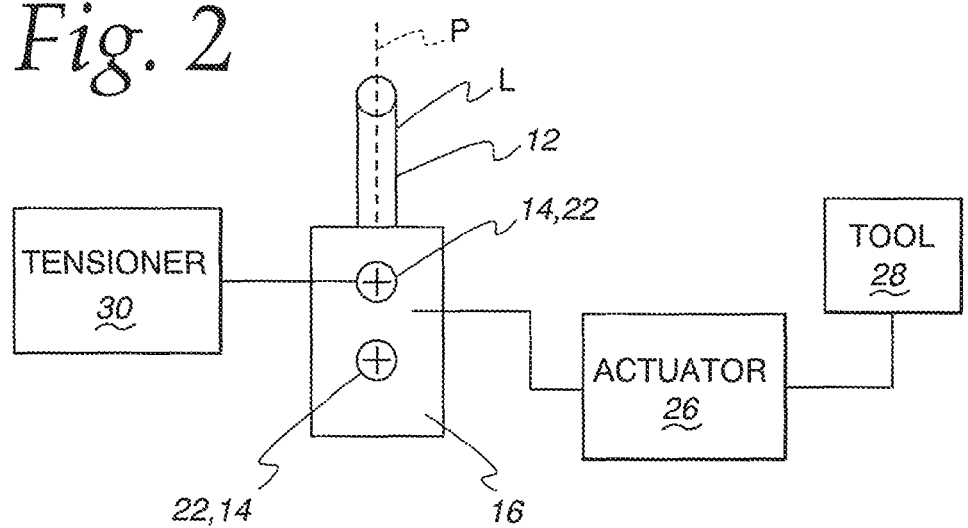
FIG. 2 is a partially schematic representation of the cable system of FIG. 1 and showing an exemplary loop.
Figure 3:
FIG. 3 is a view as in FIG. 2 from a different perspective.

The locking body 16 defines a receiver 20 for a first portion 22 of the length of cable 12 that is formed into a first loop L, as seen additionally in FIGS. 2 and 3, that resides generally in a first plane P.

A locking structure 24 on the body cooperates with the first portion 22 of the cable 12 within the receiver so as to maintain the loop L in a tensioned state. The locking structure 24 has a locked state and a released state.

The locking structure 24 includes an actuator 26 that is operable to change the locking structure selectively: a) from the released state into the locked state to thereby maintain the tensioned state of the first loop; and thereafter b) from the locked state into the released state to thereby allow tension on the length of cable to be reduced and the first loop L to be reconfigured to define a second loop that is the same as, or different than, the first loop in terms of effective diameter, number of turns, and/or tension.

The cable system could be alternatively constructed so that it cannot be changed from the locked state back into the released state.

The actuator 26 is configured to be operated by a tool 28 that can be directed from a separated position into an operative position relative to the actuator along a line or in a plane that is substantially parallel to the first plane P.

In the operative position, the tool 28 is preferably repositionable to operate the actuator 26 and change the state of the locking structure 24 without tilting the tool 28 significantly out of a plane that is parallel to the first plane P.

As shown in FIG. 2, the cable system 10 incorporates a tensioner 30 that can be engaged with the first end 14 and/or first portion 22 of the cable 12 to effect tensioning thereof preparatory to changing the locking structure 24 from the released state into the locked state. This tensioning is effected by exerting a force on the first end 14 and/or first portion 22 along a line substantially parallel to the first plane P.

With the depicted arrangement, the length of cable 12 can be introduced through a relatively small incision, formed into a loop, tensioned, and locked through manipulations that occur substantially in the same plane. Accordingly, the cable system 10 is capable of being utilized with a relatively small incision so that the overall process is minimally invasive.

Another significant aspect of the invention is the ability to pass the length of cable 12 in either direction around a bone, or the like, and then effect tensioning and locking thereof. At the same time, in one form, the inventive cable system 10 can be reconfigured once the initial cable locking occurs to subsequently allow the length of cable to be loosened, re-tensioned and re-locked with the same or a different diameter and/or with a different tension.

The schematic depictions in FIGS. 1-3 are intended to encompass a wide range of different structures consistent with the inventive concepts herein. While specific embodiments will be described hereinbelow, one skilled in the art would be capable of deriving many different variations of cable systems, consistent with the invention, that could be introduced through a single point of entry with cable tensioning and locking occurring by manipulations and component movements substantially in the same plane.

Specific forms of the cable system 10 will now be described, with it being understood that these specific forms are exemplary in nature only.

Figure 4:
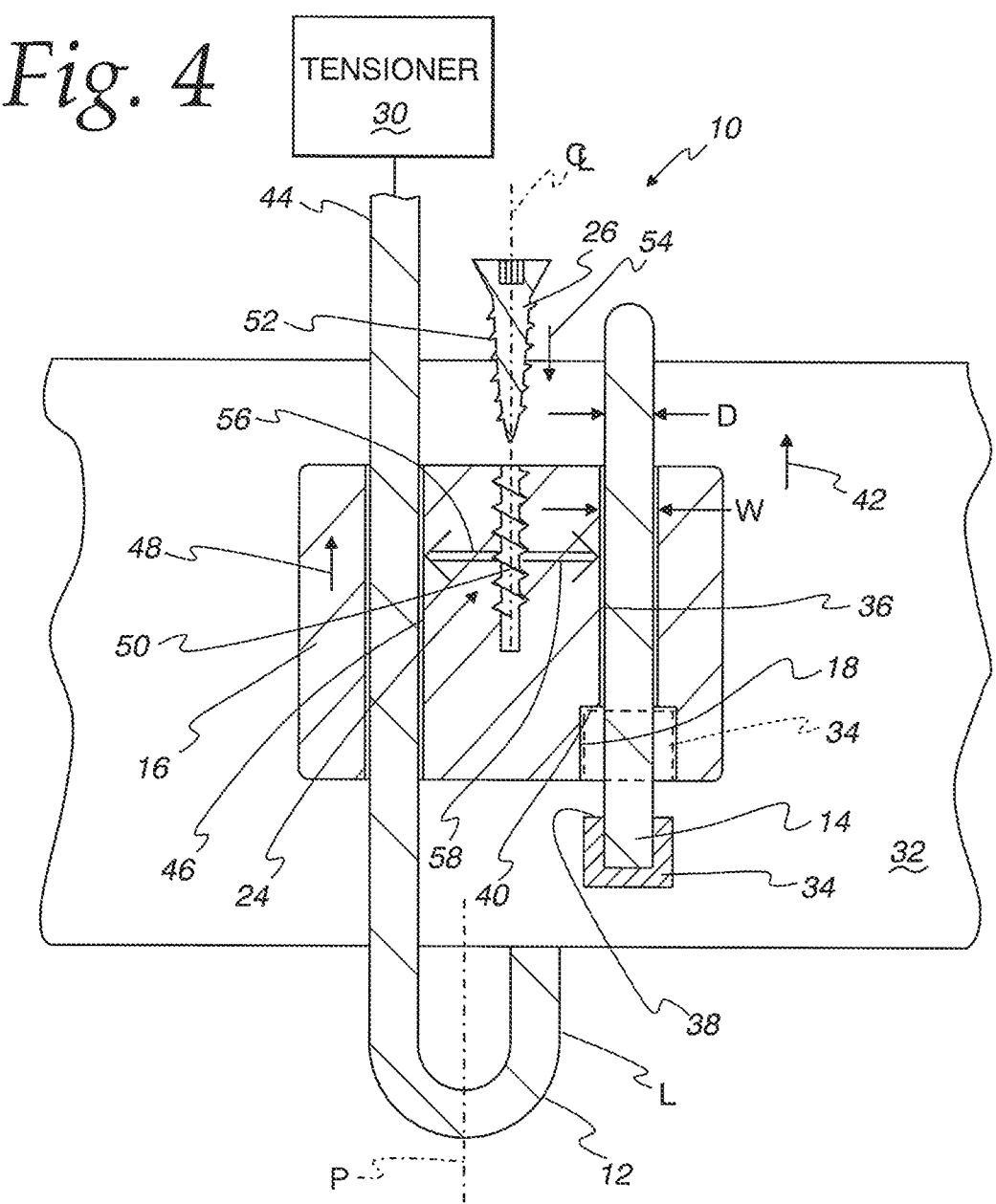
FIG. 4 is a fragmentary view of a portion of a bone with a specific form of the cable system of FIG. 1 in association therewith and the cable formed in a loop around the bone and a locking structure for the cable in a released state.
Figure 5:
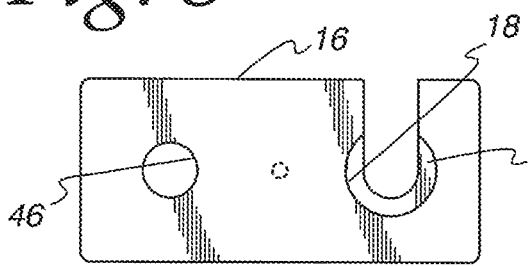
FIG. 5 is an end view of a locking body on the cable system in FIG. 4.
Figure 6:
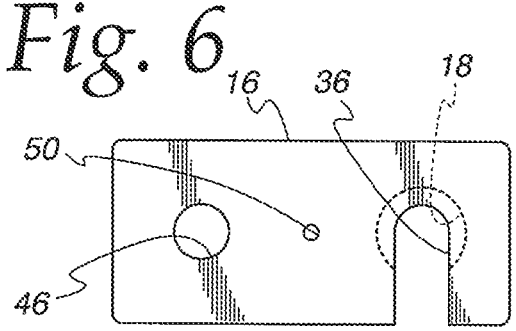
FIG. 6 is a view of the locking body from the end opposite that in FIG. 5.

In FIGS. 4-6, a cable system 10 is shown with the length of cable 12 wrapped around a length of bone 32. In FIG. 4 there is more than a single turn of the cable 12. Even with multiple turns, in the loop configuration, the overall cable loop L, with the multiple turns, can be considered to reside generally within the aforementioned plane P.

The locking body 16 is shown with a generally squared shape, though this is not required. The body 16 is cut out or initially formed so that the seat 18 is defined therein with a substantially cylindrical shape. The seat 18 is nominally matched to an anchoring element 34 that is crimped to the first cable end 14 to be permanently attached thereto.

The seat 18 is contiguous with a channel 36 with a width W slightly greater than the diameter D of the cable 12. With this arrangement, the anchoring element 34 can be directed into the seat 18 at the same time the adjacent portion of the cable 12 is directed into the channel 36. With the first cable end 14 operatively located, as shown in FIG. 3, and with the anchoring element 34 in the dotted line position, a surface 38 on the anchoring element 34 abuts to an interrupted, annular shoulder 40 on the body 16 at the transition between the channel 36 and seat 18 to thereby limit further movement of the anchoring element 34 in the direction of the arrow 42 in FIG. 4.

With the loop L formed, the opposite cable end 44 can be directed through a throughbore 46 in the locking body 16 in the direction of the arrow 48 in FIG. 4. The exposed cable end 44 can be engaged by the tensioner 30 to thereby draw and place the cable 12 in the tensioned state. Once the tensioned state therefor is achieved, the locking structure at 24 is utilized to maintain the loop L in this tensioned state.

The locking body 16 has a bore 50 extending generally parallel to the throughbore 46 and channel 36 and residing therebetween. The actuator 26, that is part of the locking structure 24, is shown in the form of a threaded screw/bolt. The screw/bolt 26 has an externally threaded body 52 that is dimensioned relative to the bore 50 so that as it is advanced by turning in the direction of the arrow 54 in FIG. 4, a wedging action is produced, thereby urging portions of the body 16 oppositely from the center line CL of the bore 50, as indicated by the arrows 56, 58, towards the separate portions of the cable 12 within the throughbore 46 and channel 36. This action squeezes the cable 12 at the locations where it resides within the throughbore 46 and channel 36 to effect locking thereof relative to the body 16. The actuator 26 thus doubles as a wedging component.

This wedging action may be made possible by making the body 16 from a compressible material that will deform as the threaded screw/bolt 26 is advanced in the direction of the arrow 54. The body 16 may be made from an appropriate metal or non-metal material.

Portions of the body 16 may be strategically removed to facilitate shifting or deformation of other portions of the body oppositely away from the bore 50 to lock the portions of the cable 12 within the throughbore 46 and channel 36, to place the locking structure 24 in the locked state therefor.

With the locking structure in the locked state, the threaded screw/bolt 26 can be backed out. This progressively releases the wedging pressure to allow the locking structure 24 to reassume the released state wherein the cable 12 is slidable within the throughbore 46 and channel 36, thereby allowing the loop L to be reconfigured and, if appropriate, re-tensioned.

Figure 7:
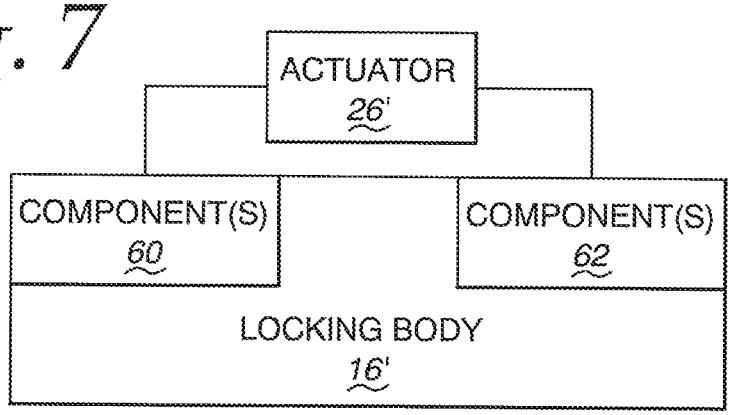
FIG. 7 is a schematic representation of a modified form of locking body.

As an alternative to relying on the deformable nature of the material making up the body 16, as shown in FIG. 7, a modified form of locking body 16' may incorporate one or more discrete, movable components 60, 62 that make up part of the locking structure. If both components are utilized, they may be shifted oppositely to be forcibly pressed against the cable within the throughbore 46 and channel 36 as the actuator 26' is advanced or otherwise repositioned to change the state of the locking structure. The components 60, 62 may be normally biased to a position wherein they do not forcibly capture the cable 12, whereupon backing of the actuator 26' out will allow the released state for the locking structure in FIG. 7 to be automatically realized.

Alternatively, only one movable component 60, 62 may be utilized for operation by the actuator. The one component 60, 62 may be moved to bear against one part/discrete length of the cable that may be forcibly urged against the body 16' or another part/discrete length of the cable.

Figure 8:
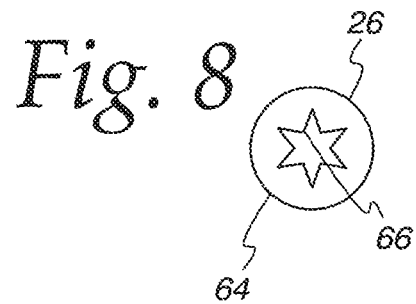
FIG. 8 is an end view of an actuator for the locking structure on the inventive cable system.

The threaded screw/bolt 26, shown in FIG. 8, may have an enlarged head 64 with a female receptacle 66 to accept a conventional turning tool, such as a torx-type, or any other type, of screwdriver. The head 64 may be configured to accept any type of turning tool, be it in the form of a screwdriver or a wrench.

As noted above, the turning of the actuator 26 about the center line CL makes possible the maintenance of the tool 28 substantially in line with the aforementioned plane P.

Figure 9:
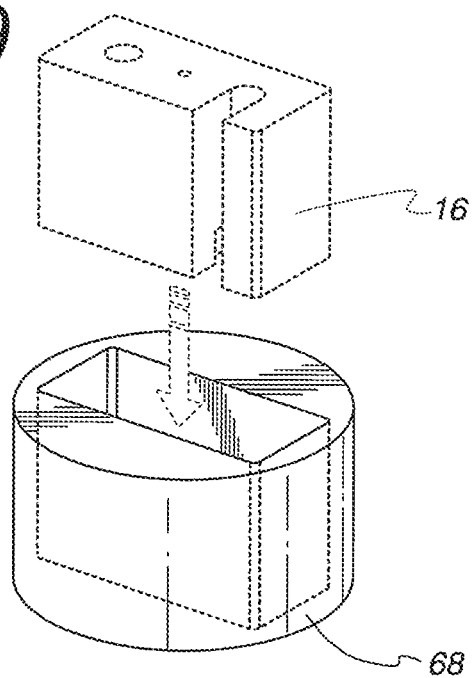
FIG. 9 is an exploded, perspective view showing an optional sleeve that surrounds the inventive locking body.

In another variation, as shown in FIG. 9, a sleeve 68 is provided to surround the body 16, thereby to prevent expansion of the body 16 under the wedging action of the actuator 26 that might compromise the holding forces upon the cable 12. The sleeve 68 also serves to maintain the different portions of the cable 12 in a predetermined, confined space. The sleeve 68 is optional in nature.

Figure 10:
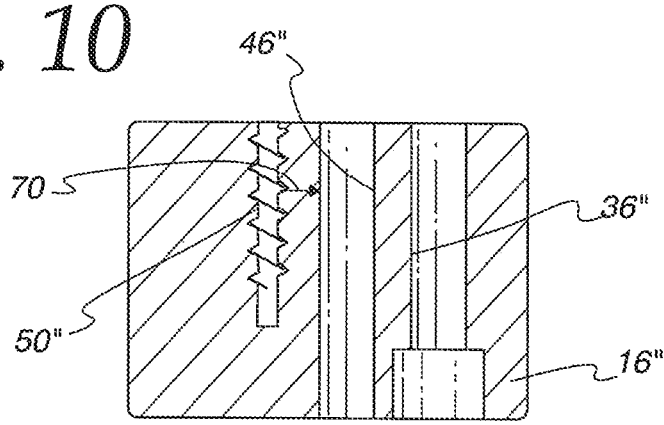
FIG. 10 is a view of a modified form of locking body taken from the same perspective as in FIG. 4.

In FIG. 10, one variation of the locking body 16" is shown wherein the channel 36" and throughbore 46" are both at the same side of the bore 50". With this arrangement, the wedging action produces a compressive force in the direction of the arrow 70 to produce the squeezing/locking action.

Figure 11:
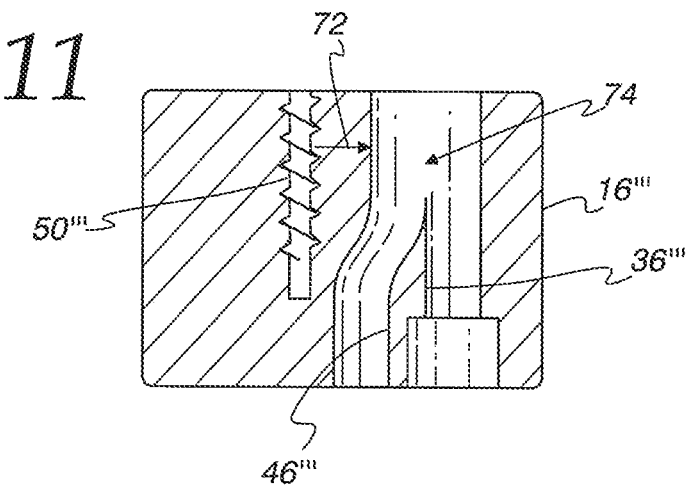
FIG. 11 is a view as in FIG. 10 of a further modified form of locking body.

In FIG. 11, a further modified form of locking body is shown at 16''', wherein the channel 36''' and throughbore $46'''$ merge on one side of the bore $50'''$ so that the wedging action in the direction of the arrow 72 squeezes the separate portions/discrete lengths of the cable 12 directly against each other within a receptacle region at 74 wherein the throughbore $46'''$ and channel $36'''$ are merged.

It should be understood that it is only necessary to wedge the cable 12 in the throughbore 46 since the cable end 14 will be held in place, with the anchoring element 34 borne against the shoulder 40 under the applied cable tension. The cable end 14 is thus effectively locked against shifting lengthwise of the cable in the channel 36. However, to increase the integrity of the locking, the cable 12 may be likewise captively held within the channel 36 under the wedging forces produced by the threaded screw/bolt 26.

Figure 12:
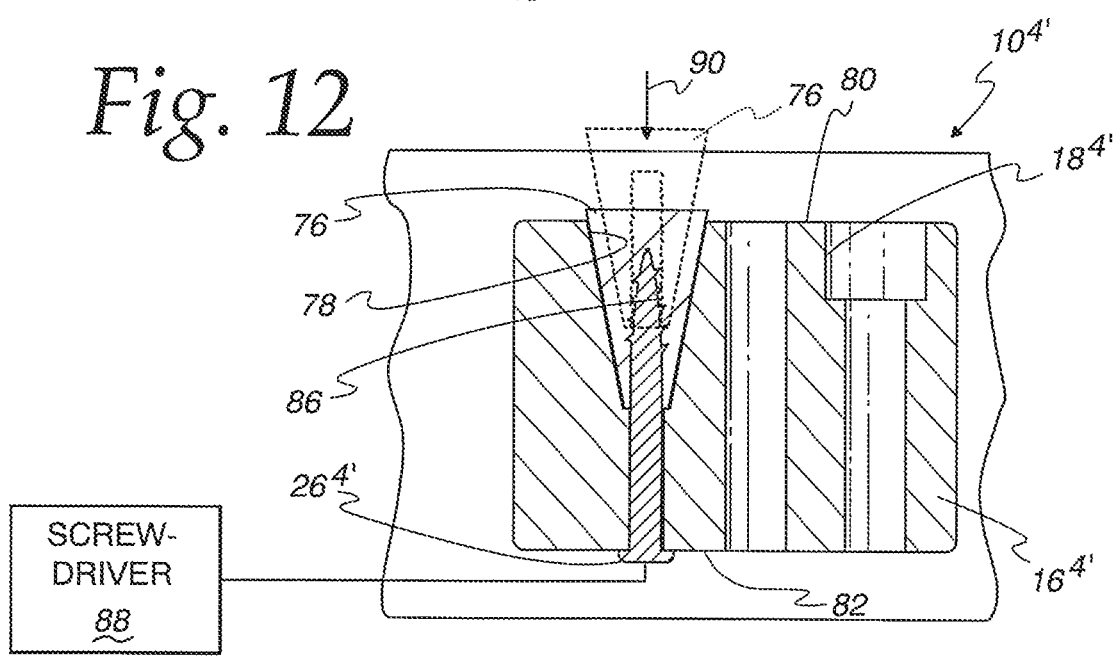
FIG. 12 is a view generally as in FIG. 4 and showing a modified form of locking body including a separate wedging component.

In FIGS. 12 and 13, a modified form of cable system is shown at $10^{4'}$. Instead of relying upon a threaded screw/bolt to directly cause deformation of the body, the body $16^{4'}$ is configured to accommodate a separate wedging component 76 that is part of the locking structure and placed within a complementary bore 78 in the body $16^{4'}$. In this embodiment, the wedging component 76 is introduced to the bore 78 from one side 80 of the body $64^{4'}$, with the threaded screw/bolt $26^{4'}$ introduced from the opposite side 82 of the body $16^{4'}$ so that a threaded portion 84 on the threaded screw/bolt $26^{4'}$ engages within a bore 86 in the wedging component 76. As the threaded screw/bolt $26^{4'}$ is turned, as by a screwdriver 88, the wedging component 76 moves in the direction of the arrow 90 from the dotted line position towards the solid line position therefor in FIG. 12. The threaded portion 84 has a tapered shape that causes a bifurcated end 92 on the wedging component 76 to reconfigure so that spaced portions 94, 96 thereon, between which the bore 86 is formed, spread outwardly, as indicated by the arrows 98, 100.

This wedging action is utilized to lock the cable 12 as in all of the earlier described embodiments. The wedging component 76 is shown in FIG. 12 with the body $16^{4'}$ having a configuration similar to that shown in FIG. 10, with the exception that the seat $18^{4'}$ opens oppositely to the direction of introduction of the wedging component 76.

A similar wedging component could be used in either the embodiments shown in FIGS. 4 and 11.

As an alternative to requiring that the wedging components themselves be deformed, the wedging action might be produced instead by the translation of the wedging component, as shown in FIGS. 14 and 15. In FIG. 14, a body $16^{5'}$ is shown with a bore $78^{5'}$ for reception of a wedging component $76^{5'}$. The bore $78^{5'}$ is shown with a constant diameter D1, whereas the outer surface 102 of the wedging component $76^{5'}$ is tapered to cause the requisite wedging action to be produced as the wedging component $76^{5'}$ drawn into the bore $78^{5'}$ the direction of the arrow 104.

In an alternative form, as shown in FIG. 15, the bore $78^{6'}$ in the body $16^{6'}$ tapers correspondingly to the outer surface $102^{6'}$ of the wedging component $76^{6'}$. However, the taper angle for the bore $78^{6'}$ is less than for the outer surface $102^{6'}$ so that the requisite wedging action is produced as the wedging component $76^{6'}$ is advanced in the direction of the arrow 106.

With the last embodiments, the wedging components may directly deform their associated bodies to produce the locking action upon the cable 12 or alternatively might cooperate with one or more movable components on the locking body to accomplish this.

It should be understood that the invention contemplates many variations from the structures depicted to produce the wedging action. The invention contemplates that any insertable or movable component that wedges to produce the captive holding/locking force upon the cable might be utilized. As an example, the bore receiving the threaded screw/bolt may be of a relatively constant diameter with the screw/bolt tapered. The bore might be alternatively configured to progressively enlarge as the screw/bolt is advanced.

Further, it is not required that the wedging component have an outer surface with a taper as shown in FIGS. 13-15. As shown, for example, in FIG. 16, the wedging component $76^{7'}$ has sides 108, 110 that are substantially parallel. As the threaded screw/bolt is directed into the bore $86^{7'}$, the portions 112, 114 bounding the bore $86^{7'}$ spread oppositely in the direction of the arrows 116, 118 to produce the requisite wedging forces.

It should also be understood that the wedging components can be introduced to a bore within the respective locking bodies so as to be surrounded by the body. Alternatively, the bores may be open on one or two sides so long as they remain at all times together with the locking bodies, with the locking structures in both locked and released states.

Figure 17:
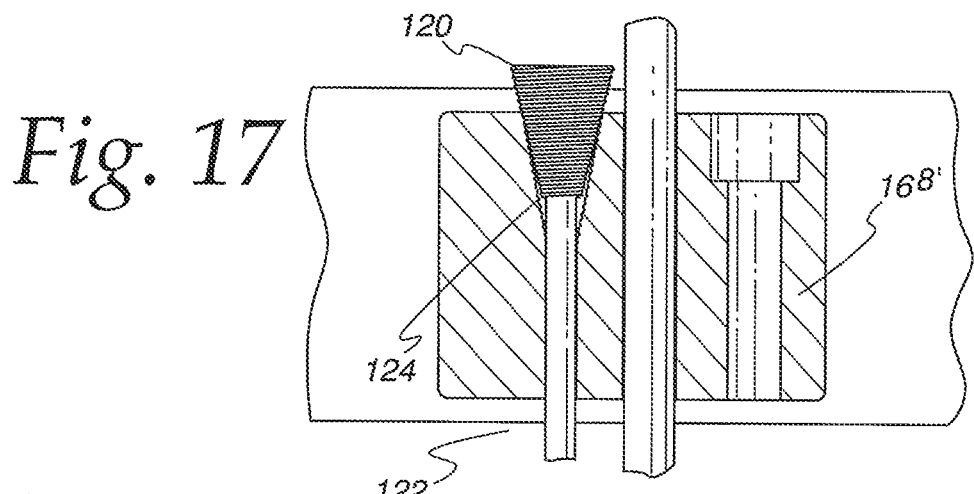
FIG. 17 is a view as in FIG. 12 of a further modified form of cable system and with a threaded wedging component, with the wedging component situated to place the locking mechanism in a released state.
Figure 18:
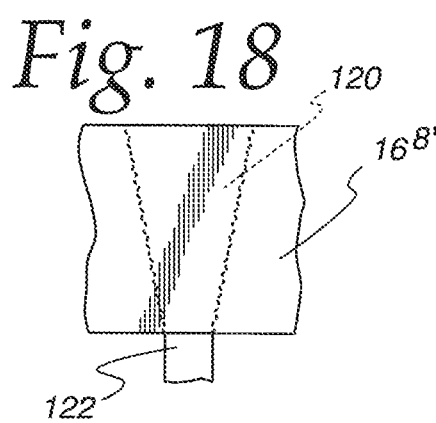
FIG. 18 is a fragmentary view as in FIG. 17 with the wedging component situated to place the locking mechanism in a locked state.

An alternative form of cable system is shown in FIGS. 17 and 18. In FIGS. 17 and 18, a body $16^{8'}$ is shown similar to that in FIG. 12, with the exception that a tapered wedging component/actuator 120 is directly engaged and turned by a tool 122 that is initially directed through the body $16^{8'}$ to engage the end 124 of the wedging component 120. The end 120 has a fitting adapted to accept a tool that is used to turn the wedging component/actuator 120. By turning the wedging component/actuator 120, it is changed from the FIG. 17 position into the FIG. 18 position, wherein it wedges within the body $16^{8'}$ to lock the cable as in prior embodiments. The wedging component/actuator 120 may be alternatively situated between portions of the cable that are locked.

The threads on the wedging component/actuator 120 may be left-hand threads so that a surgeon would turn the wedging component/actuator 120 as he/she would a right-handed thread from the opposite side.

Figure 19:
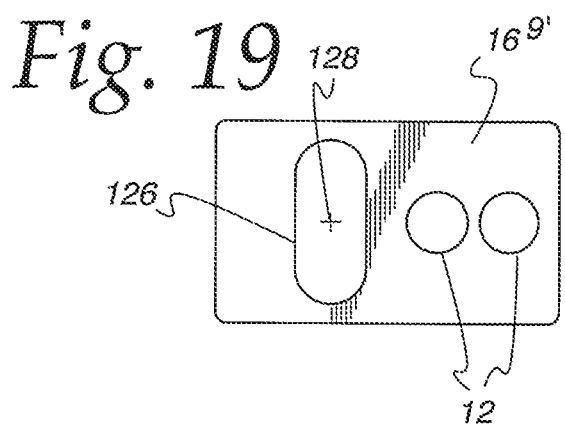
FIG. 19 is an end view of a modified form of locking body with a wedging component/actuator situated so that the locking mechanism is in a released state.
Figure 20:
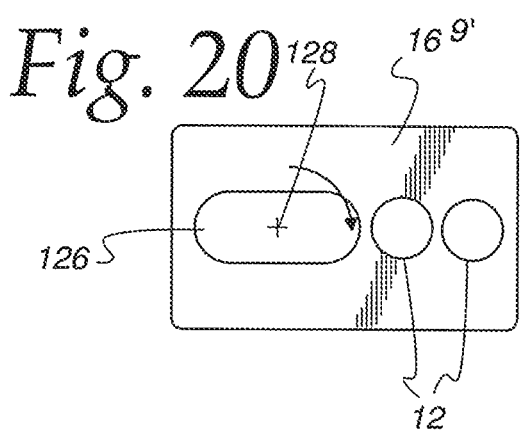
FIG. 20 is a view as in FIG. 19 wherein the locking mechanism is in a locked state.
Figure 21:
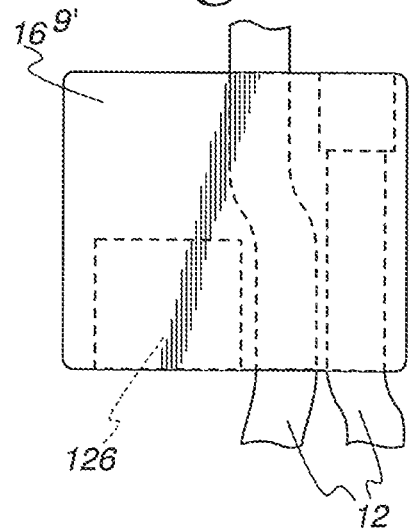
FIG. 21 is a view of the components in FIG. 20 from a different perspective.

In FIGS. 19-21, a further alternative form of cable system is shown with a body $16^{9'}$ is configured to accept a wedging component/actuator 126 that has an oval shape in cross-section. The wedging component/actuator 126 can be turned around its central axis 128 from the position shown in FIG. 19, representing the released state for the locking mechanism, to the position shown in FIGS. 20 and 21, representing the locked state for the locking mechanism. As the wedging component/actuator 126 is turned, the separate discrete lengths of the cable 12, running substantially parallel to each other within the body $16^{9'}$, are urged towards each other to be captively held and locked in the FIG. 20 position.

Figure 22:
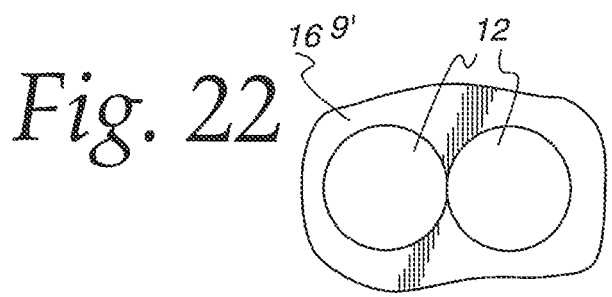
FIG. 22 is a fragmentary view showing cable portions wedged against each other through the components shown in FIGS. 19-21.

As shown in FIG. 22, the components in FIGS. 19-21 may be configured so that the discrete cable lengths are urged radially against each other.

With the embodiment shown in FIGS. 19-21, the wedging component/actuator 126 has an extended surface length parallel to the cable portions within the body $16^{9'}$. It is not necessary that the shape be exactly oval. A tapered cam surface could be provided with variable thickness. Regardless of the details, the extended contact area produces a positive holding force upon the cable portions. With this arrangement, there is no force generated by the cable that would produce a significant component tending to turn the wedging component 126 from the position shown in FIGS. 20 and 21, representing the locked state for the locking mechanism.

With all of the embodiments described above, the cable 12 can be passed in either direction through the locking bodies with the locking structures in a released state. The anchoring element can then be seated, whereupon the free end of the cable 12 can be passed through the body to a tensioner. Once the desired tension is generated, the locking structure is placed in its locked state.

All of the various wedging components can be designed to act directly against the cable 12 within the body or against an intermediate, separate, movable component or an integral part of the body that merely flexes under the wedging forces. In the event that the wedging components are abutted directly to the cable, they are ideally provided with a smooth surface so as to avoid cutting or nicking that ultimately may lead to a failure of the cable.

Figure 23:
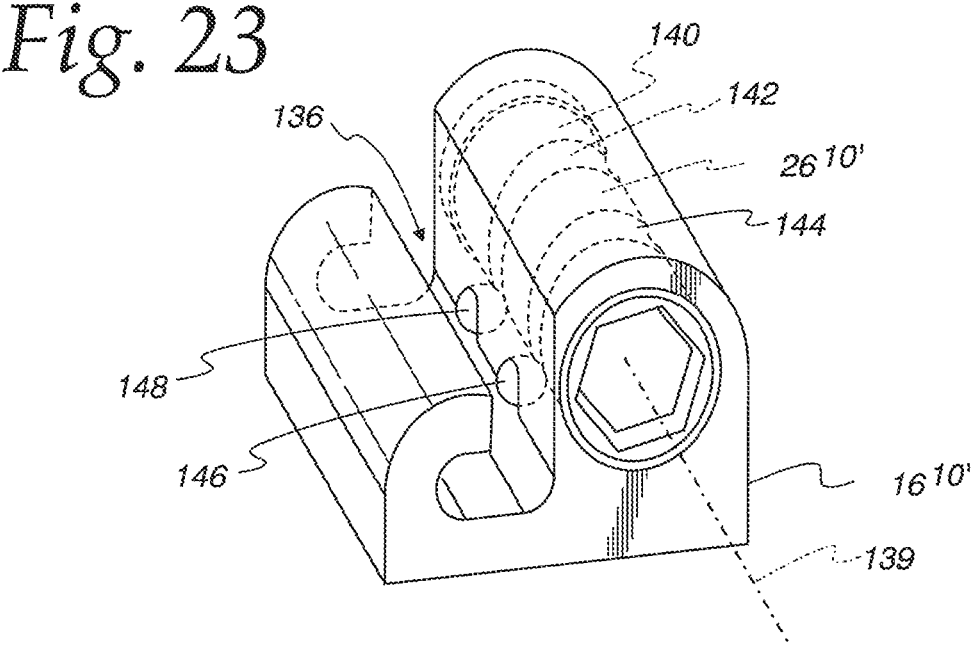
FIG. 23 is a perspective view of a modified form of locking body, according to the present invention, and including an actuator that is turned to lock cable portions through movable, discrete components.
Figure 24:
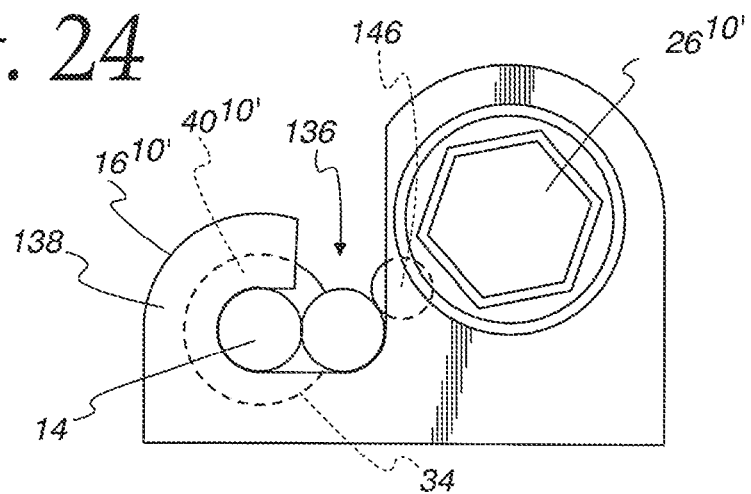
FIG. 24 is an end view of the components in FIG. 23.

In FIGS. 23 and 24, a modified form of locking body is shown at $16^{10'}$. The locking body $16^{10'}$ has a receptacle 136 that receive both cable portions that would otherwise be separated, as in the aforementioned throughbore 46 and channel 36. The body $16^{10'}$ defines a wall 138 with a shoulder $40^{10'}$ to abut to the anchoring element 34 on the cable end 14.

In this embodiment, the actuator $26^{10'}$ is guided in movement relative to the body around an axis 139. The actuator has a cylindrical body 140 with separate grooves 142, 144 at axially spaced locations.

Discrete wedging components 146, 148, that may be ball-shaped or otherwise configured, reside, one each, in the grooves 142, 144. The components 146, 148 are captive between the actuator body 140 and the cable portions within the receptacle 136.

The grooves 142, 144 have a varying radial depth. By turning the actuator $26^{10'}$ in one direction, the components 146, 148 are progressively urged against the cable portions within the receptacle 136 to effectively lock the same against each other and the portion of the body $16^{10'}$ bounding the receptacle 136. By reversely turning the actuator $26^{10'}$, the cable portions are released and can be slid lengthwise of the cable within the receptacle 136.

Figure 25:
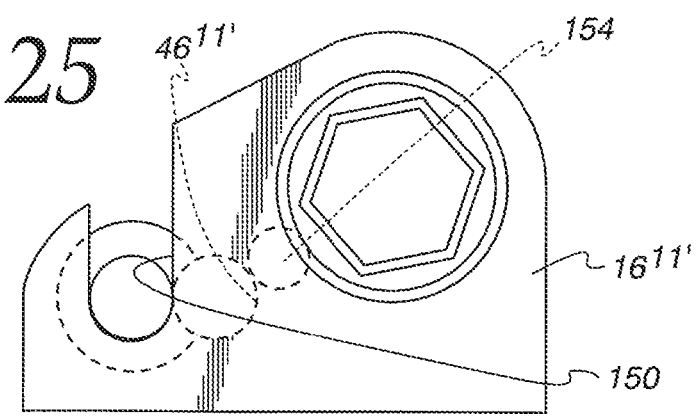
FIG. 25 is a view as in FIG. 24 showing a structure as in FIGS. 23 and 24 with a modified form of locking body.
Figure 26:
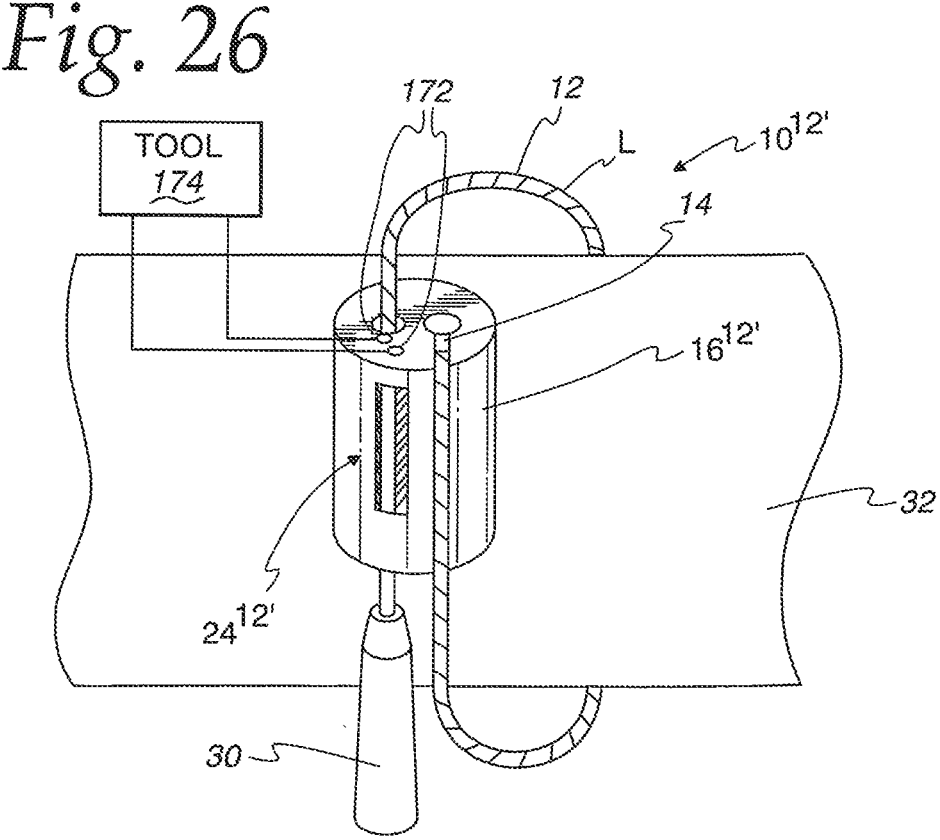
FIG. 26 is a view as in FIG. 4 of a modified form of cable system including a locking body with a locking system thereon.
Figure 27:
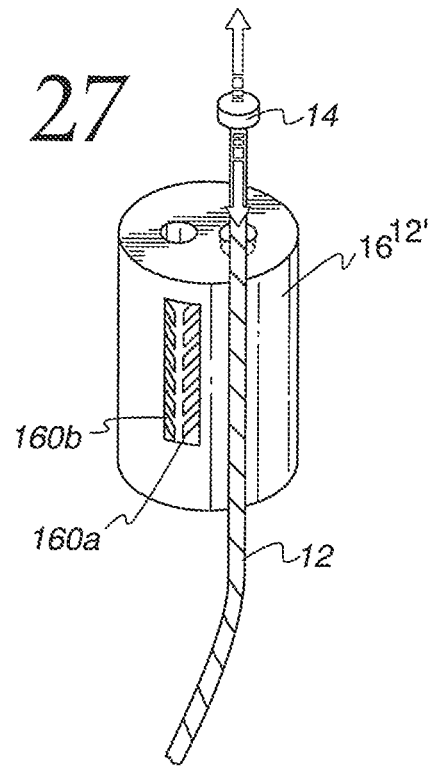
FIG. 27 is a perspective view of the cable system in FIG. 27 and showing a cable end separated from the locking body.
Figure 28:
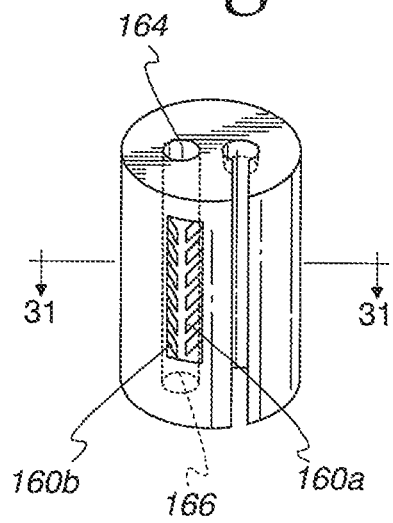
FIG. 28 is a perspective view of the locking body.
Figure 41:
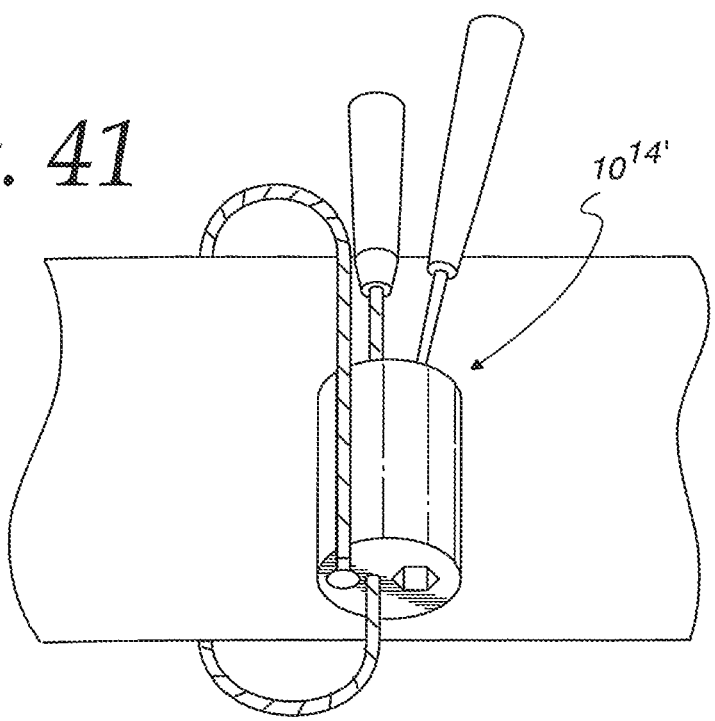
FIG. 41 is a view as in FIG. 34 of a further modified form of cable system, according to the invention, including a locking body and locking system.
Figure 42:
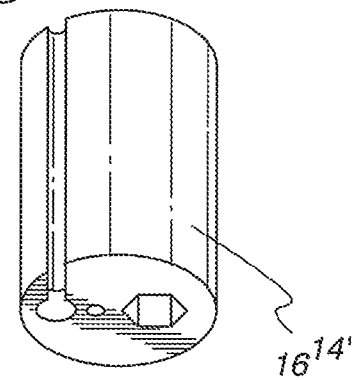
FIG. 42 is a perspective view of the locking body in FIG. 41.
Figure 43:
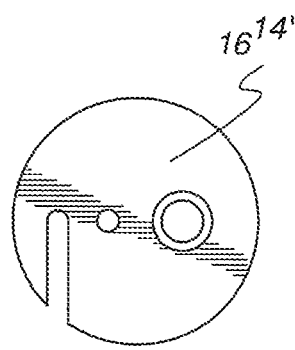
FIG. 43 is a view of the locking body taken from one end thereof.
Figure 44:
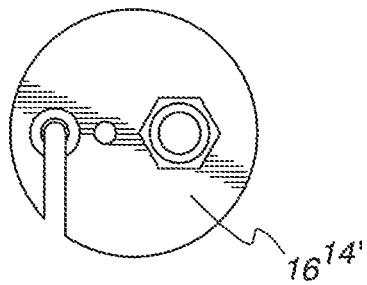
FIG. 44 is a view of the locking body taken from the end opposite that in FIG. 43.
Figure 45:
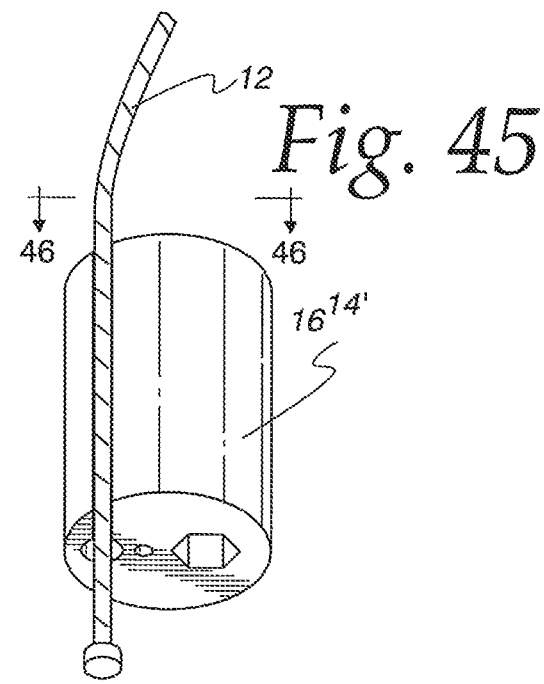
FIG. 45 is a perspective view of the cable system with one cable end separated from the locking body.

A modified form of the body in FIGS. 23 and 24 is shown at $16^{11'}$ in FIG. 25. The primary difference between the body $16^{11'}$ and the body $16^{10'}$ is that the body $16^{11'}$ has a divider 150 that maintains the cable portions spaced from each other. Accordingly, the components 154 (one shown), corresponding to the components 146, 148, bear only upon the cable portion within the receptacle/throughbore $46^{11'}$.

In FIGS. 26-33, a further modified form of cable system is shown at $10^{12'}$ with a locking body $16^{12'}$ with an associated cable 12 shown wrapped around a length of bone 32. The first cable end 14 is joined to the body $16^{12'}$ as in earlier described embodiments.

The first portion 22 of the length of cable 12 that resides within the locking body $16^{12'}$ cooperates with a plurality of tines 160a, 160b that make up a locking structure $24^{12'}$. Each of the tines 160a, 160b is cantilever mounted within a body chamber/receiver 162, with the tines 160a projecting towards the tines 160b, and vice versa. The chamber 162 is enlarged between, and contiguous with, end openings 164, 166 through which the cable 12 is extended.

The tines 160a, 160b cooperate with the cable portion 22 in like fashion. Exemplary tines 160a, in a relaxed state, project radially but may be slightly axially declined, as shown in dotted lines in FIG. 33. Each of the tines 160a has a free edge 168a.

As shown in FIG. 33, as the cable 12 is advanced in the direction of the arrow 170 into and through the chamber 162, the cable 12 engages the tines 160a and bends them down, as shown in FIG. 32 and in solid lines in FIG. 33. By reason of the tines 160a being bent and configured as shown, the free edges 168a will engage and dig into the cable 12 to prevent movement of the cable 12 oppositely to the direction of the arrow 170. Residual loading forces urge the free edges 168a positively against the cable 12.

Accordingly, the cable 12 can be advanced in only one direction through the chamber 162 and relative to the tines 160a, 160b. The tines 160b cooperate in the same manner with the cable 12 at diametrically opposite locations. The tines 160a, 160b are also mutually reinforcing to keep the cable 12 stably centered within the chamber 162 and positively block any movement of the cable 12 opposite to the direction of the arrow 170 within the chamber 162.

Accordingly, through the tensioner 30, the mere act of drawing the cable 12 along a line, within or parallel to the plane of the cable loop L, changes the locking structure $24^{12'}$ into different locked states to thereby maintain a tensioned state of the cable loop.

In other words, the tines 160a, 160b act as individual actuators that are operable in response to movement of the cable 12 thereagainst to change the locking structure $24^{12'}$ from an initially released state, before the cable 12 engages the tines 160a, 160b, into different locked states.

Optional access openings 172 may be provided to admit components on a tool 174 that can be used to reposition the tines 160a, 160b, thereby changing the locking structure $24^{12'}$ from the locked state into a released state, wherein the previously tensioned cable loop L can be loosened.

The tines may be made from metal or other suitable material that will withstand the anticipated forces applied thereto.

The tensioner 30 can be moved in a line that is parallel to the plane of the loop L to engage the cable 12 and thereafter effect the cinching of the bone 32.

In FIGS. 34-40, a further modified form of cable system is shown at $10^{13'}$. The cable system $10^{13'}$ consists of a locking body $16^{13'}$ that cooperates with the cable 12, as previously described.

The locking body $16^{13'}$ cooperates with the cable 12 at the cable end 14 in the same manner as for other embodiments described herein.

The locking body $16^{13'}$ defines a chamber/receiver 176 within which a wedging component 178 is located. The wedging component 178 is movable between a first position, as shown in solid lines in FIG. 39, and a second position, as shown in dotted lines in that same Figure and in solid lines in FIG. 40 by pivoting against and relative to the locking body $16^{13'}$ about an axis at only one of two ends E1, E2 spaced along the actuator axis. Through this arrangement, the wedging component 178 can be moved towards and away from the cable length DL2.

The first cable portion 22 that resides within the receiver/chamber 176 consists of separate discrete lengths DL1, DL2 of the cable 12 that reside in close proximity to each other with the configuration of the loop L selected and tensioned through the tool 30, as in prior embodiments. The discrete length DL2 is formed on a part of the cable 12 that extends between opposite openings 180, 182 that are in communication with each other through the chamber 176.

An actuator $26^{13'}$ has a threaded portion 184 that is threadably engaged within a bore 186. By turning the actuator $26^{13'}$ about its axis, the actuator $26^{13'}$ can be advanced in the direction of the arrow 188. As this occurs, the actuator $26^{13'}$ initially contacts a wall surface 190 on the wedging component 178, which is at an angle to a surface 192 on the locking body $16^{13'}$ that bounds the bore 186. Continued turning of the actuator $26^{13'}$ advances the same against the converging surfaces 190, 192 to progressively wedge the component 178 from its first position into its second position, wherein it squeezes the discrete cable length DL2 against the discrete cable length DL1 and in turn against a surface 194 on the locking body 16$^{13'}$.

The wedging component 178 may be normally biased into its first position through any suitable biasing structure 195, whereby upon retraction of the actuator 26$^{13'}$, the wedging component 178 moves back towards its first position to allow the cable tension to be released. Alternatively, the wedging component 178 can be movable freely between its first and second positions without any biasing force. Through repositioning of the actuator 26$^{13'}$, the wedging component 178 can be changed between its first and second positions.

The wedging component 178 has a gradually curved, convex surface 196 to directly engage the cable 12 with the wedging component 178 in its second position, corresponding to the locked state for the locking structure 24$^{13'}$. This rounded surface configuration extends the length where the discrete wire lengths DL1, DL2 are held together for positive securement and also avoids localized pinching as might damage the cable 12 and potentially precipitate its failure.

The threaded portion of the actuator 26$^{13'}$ is shown as tapered so that the actuator itself acts as a wedging component. The required wedging action could be produced without the taper.

In FIGS. 41-47, a further modified form of cable system is shown at 10$^{14'}$ with a locking body 16$^{14'}$ with an overall construction similar to that of the locking body 16$^{13'}$, previously discussed.

The primary distinction between the cable system 10$^{14'}$ and the earlier described cable system 10$^{13'}$ is that the cable system 10$^{14'}$ uses a different form of actuator 26$^{14'}$ and wedging component 198, corresponding to the wedging component 138 on the cable system 10$^{13'}$, in a chamber/receiver 200, corresponding to the chamber/receiver 176.

The actuator 26$^{14'}$ consists of a threaded body 202 with an enlarged head 204. The head region is countersunk in a wall portion 206. The body 202 is threaded into a slider 208 that moves guidingly back and forth along the central axis 210 of the actuator 26$^{14'}$ without turning around the axis 210. The actuator 26$^{14'}$ thus moves only by turning around the axis 210 and does not shift in an axial direction as it is turned.

The wedging component 198 is in the form of a leaf spring, with ends 212, 214 fixed to the wall portion 206 and slider 208, respectively. As the actuator 26$^{14'}$ is turned in one direction, the slider 208 moves guidingly towards the head 204, thereby changing the wedging component 198 from a first shape, as shown in FIG. 46, eventually to a second shape, as shown in FIG. 47. As this occurs, the locking structure 24$^{14'}$ is changed from its released state into its locked state.

In the locked state, the wedging component 198 bears discrete lengths DL1, DL2 of the cable 12 against each other and in turn against a locking body surface 216.

The wedging component 198 has a gradually curved, convexly-shaped surface 199 to bear against the cable 12, which has the advantages as explained with respect to the wedging component 178 in the prior embodiment.

By reversely turning the actuator 26$^{14'}$, the wedging component 198 is changed from the FIG. 47 configuration back towards its relaxed configuration in FIG. 46, thereby changing the locking structure 24$^{14'}$ from the locked state back into the released state.

A still further form of cable system, according to the invention, is shown at 10$^{15'}$ in FIGS. 48-54. The cable system 10$^{15'}$ has a locking system 24$^{15'}$ on the locking body 16$^{15'}$ that incorporates aspects of the locking systems 24$^{13'}$ and 24$^{14'}$.

More specifically, the locking system 24$^{15'}$ utilizes the same configuration of actuator 26$^{15'}$ as in the locking system 10$^{14'}$, with the threaded body 202 and guided slider 208.

The slider 208 acts against a cam surface 218 on a wedging component 220 that is movable between a first position, as shown in FIG. 53, and a second position, as shown in FIG. 54. As the wedging component 220 is changed between its first and second positions through the actuator 26$^{15'}$, the locking structure 24$^{15'}$ is changed between its released states and locked states.

With the locking system 24$^{15'}$ in its locked state, a convexly curved surface 222 on the wedging component 220 bears against discrete lengths DL1, DL2 of the cable 12, bearing them forcibly against each other and a surface 224 of the locking body 16$^{15'}$.

As with the wedging component 178, the wedging component 220 may be biased normally into its first position or, alternatively, loosely held therein. In either event, the locking system 24$^{15'}$ can be changed back and forth between locked and released states through turning of the actuator 26$^{15'}$ about its lengthwise axis 226.

With each of the locking systems 10$^{12'}$, 10$^{13'}$, 10$^{14'}$, 10$^{15'}$, as in the others described above, the cable 12 can be passed in either direction around the bone.

Securing of the cable 12 in each case is effected after the cable 12 has been passed around the bone.

The cable end 14 in each embodiment can be simply press fit in place to brace the cable against a force that produces tension. The cable end 14 can be readily separated, as in the event that the cable 12 is to be replaced.

In all of the locking system versions, the actuators can be engaged through movement of a tool along a line parallel to the plane of the cable loop L and repositioned by movement around and/or along an axis that is parallel to the plane of the cable loop L. This permits a minimally invasive approach to the bone for fixation. As a result, the accommodating incision can be made relatively small, whereas operation in transverse planes requires a significantly larger incision through which procedures are performed using a cable.

The foregoing disclosure of specific embodiments is intended to be illustrative of the broad concepts comprehended by the invention.

The invention claimed is:
1. A surgical cable system comprising:
    a length of cable having a first end; and
    a locking body for the length of cable in which the first cable end is operatively located,
    the locking body defining a receiver for a first portion of the length of cable with the length of cable formed into a first loop that resides generally in a first plane; and
    a locking structure on the locking body that cooperates with the first portion of the cable so as to maintain the first loop in a tensioned state,
    the locking structure having a locked state and a released state,
    the locking structure comprising an actuator that is operable to change the locking structure selectively from the released state into the locked state to thereby maintain the tensioned state of the first loop,
    the locking structure changeable from the released state into the locked state as an incident of one of: a) moving at least a part of the actuator at least one of along and around an axis that is generally parallel to the first plane; and b); moving a part of the cable length along a first line that is generally parallel to the first plane, wherein the locking structure comprises a wedging component that is separate from the locking body and configured to be moved by the actuator relative to the locking body to change the locking structure from the released state into the locked state, wherein the wedging component is configured to urge a discrete length of the cable, that extends generally parallel to the axis, in a manner that the discrete length of the cable resides captively between the wedging component and a surface on the locking body with the locking structure in the locked state, wherein the actuator acts directly against each of the wedging component and the locking body.

2. The surgical cable system according to claim 1 wherein the wedging component is movable as one piece relative to the locking body to change the locking structure from the released state into the locked state.

3. The surgical cable system according to claim 2 wherein the wedging component is separable from the locking body.

4. A surgical cable system comprising:
a length of cable having a first end; and
a locking body for the length of cable in which the first cable end is operatively located,
the locking body defining a receiver for a first portion of the length of cable with the length of cable formed into a first loop that resides generally in a first plane; and
a locking structure on the locking body that cooperates with the first portion of the cable so as to maintain the first loop in a tensioned state,
the locking structure having a locked state and a released state,
the locking structure comprising an actuator that is operable to change the locking structure selectively from the released state into the locked state to thereby maintain the tensioned state of the first loop,
the locking structure changeable from the released state into the locked state as an incident of one of: a) moving at least a part of the actuator at least one of along and around an axis that is generally parallel to the first plane; and b); moving a part of the cable length along a first line that is generally parallel to the first plane,
wherein the locking structure comprises a wedging component that is separate from the locking body and configured to be moved by the actuator relative to the locking body to change the locking structure from the released state into the locked state,
wherein the wedging component is configured to urge a discrete length of the cable, that extends generally parallel to the axis, captively against a surface with the locking structure in the locked state,
wherein the actuator acts directly against each of the wedging component and the locking body,
wherein the actuator has a tapered configuration that acts between the wedging component and locking body to cause an increasing wedging force as the actuator is moved,
wherein the locking structure is changeable from the released state into the locked state by moving at least a part of the actuator at least one of along and around an axis that is generally parallel to the first plane.

5. The surgical cable system according to claim 4 wherein the actuator is configured to be operated by a tool that is directed from a separated position into an operative position relative to the part of the actuator by movement of the tool in a plane that is substantially parallel to the first plane.

6. The surgical cable system according to claim 4 wherein the actuator comprises a threaded portion that is turned around an axis to change the locking structure from the released state into the locked state.

7. The surgical cable system according to claim 6, wherein the actuator comprises a wedging component that is turned around an axis to change the locking structure from the released state into the locked state.

8. The surgical cable system according to claim 4 wherein with the locking structure in the locked state, a part of the wedging component urges the first portion of the length of cable against the locking body.

9. The surgical cable system according to claim 4 wherein an anchoring element is provided on the first end of the length of cable and the locking body defines a seat for the anchoring element in which the anchoring element is blocked.

10. The surgical cable system according to claim 9, wherein the seat is bounded by a shoulder to which the anchoring element abuts and against which the anchoring element can be drawn to produce tension on the length of cable.

11. The surgical cable system according to claim 10, wherein the anchoring element can be releasably pressed into the seat to allow the length of cable to be separated from the locking body.

12. A surgical cable system comprising:
a length of cable having a first end; and
a locking body for the length of cable in which the first cable end is operatively located,
the locking body defining a receiver for a first portion of the length of cable with the length of cable formed into a first loop that resides generally in a first plane; and
a locking structure on the locking body that cooperates with the first portion of the cable so as to maintain the first loop in a tensioned state,
the locking structure having a locked state and a released state,
the locking structure comprising an actuator that is operable to change the locking structure selectively from the released state into the locked state to thereby maintain the tensioned state of the first loop,
the locking structure changeable from the released state into the locked state as an incident of one of: a) moving at least a part of the actuator at least one of along and around an axis that is generally parallel to the first plane; and b); moving a part of the cable length along a first line that is generally parallel to the first plane,
wherein the locking structure comprises a wedging component that is configured to be moved by the actuator guidingly against and relative to the locking body to change the locking structure from the released state into the locked state,
wherein the wedging component is configured to urge a discrete length of the cable, that extends generally parallel to the axis, captively against a surface with the locking structure in the locked state,
wherein the actuator acts directly against each of the wedging component and the locking body,
wherein the locking structure is changeable from the released state into the locked state by moving at least a part of the actuator at least one of along and around an axis that is generally parallel to the first plane,
wherein the locking structure is operable to change the locking structure from the released state into the locked state without reconfiguring the locking body and from the locked state into the released state to thereby allow tension on the first loop to be reduced and the first loop to be reconfigured.

13. A surgical cable system comprising:
a length of cable having a first end; and
a locking body for the length of cable in which the first cable end is operatively located,
the locking body defining a receiver for a first portion of the length of cable with the length of cable formed into a first loop that resides generally in a first plane; and
a locking structure on the locking body that cooperates with the first portion of the cable so as to maintain the first loop in a tensioned state,
the locking structure having a locked state and a released state,
the locking structure comprising an actuator that is operable to change the locking structure selectively from the released state into the locked state to thereby maintain the tensioned state of the first loop,
the locking structure changeable from the released state into the locked state as an incident of one of: a) moving at least a part of the actuator at least one of along and around an axis that is generally parallel to the first plane; and b); moving a part of the cable length along a first line that is generally parallel to the first plane,
wherein the locking structure comprises a wedging component that is separate from the locking body and configured to be moved by the actuator relative to the locking body to change the locking structure from the released state into the locked state,
wherein the wedging component is configured to urge a discrete length of the cable, that extends generally parallel to the axis, captively against a surface with the locking structure in the locked state,
wherein the actuator acts directly against each of the wedging component and the locking body,
wherein the actuator has a tapered configuration that acts between the wedging component and locking body to cause an increasing wedging force as the actuator is moved,
wherein the wedging component is movable as one piece relative to the locking body to change the locking structure from the released state into the locked state,
wherein the actuator has a threaded portion that threadably engages the wedging component and moves the wedging component relative to the locking body as the threaded portion is turned around an axis to thereby change the locking structure from the released state into the locked state.

14. A surgical cable system comprising:
a length of cable having a first end; and
a locking body for the length of cable in which the first cable end is operatively located,
the locking body defining a receiver for a first portion of the length of cable with the length of cable formed into a first loop that resides generally in a first plane; and
a locking structure on the locking body that cooperates with the first portion of the cable so as to maintain the first loop in a tensioned state,
the locking structure having a locked state and a released state,
the locking structure comprising an actuator that is operable to change the locking structure selectively from the released state into the locked state to thereby maintain the tensioned state of the first loop,
the locking structure changeable from the released state into the locked state as an incident of one of: a) moving at least a part of the actuator at least one of along and around an axis that is generally parallel to the first plane; and b); moving a part of the cable length along a first line that is generally parallel to the first plane,
wherein the locking structure comprises a wedging component that is configured to be moved by the actuator guidingly against and relative to the locking body to change the locking structure from the released state into the locked state,
wherein the wedging component is configured to urge a discrete length of the cable, that extends generally parallel to the axis, captively against a surface with the locking structure in the locked state,
wherein the actuator acts directly against each of the wedging component and the locking body,
wherein the locking structure is changeable from the released state into the locked state by moving at least a part of the actuator at least one of along and around an axis that is generally parallel to the first plane,
wherein with the locking structure in the locked state, a part of the wedging component urges the first portion of the length of cable against the locking body,
wherein with the locking structure in the locked state the wedging component urges one discrete length of the first portion of the length of cable against a second discrete length of the first portion of the length of cable and against the locking body.

15. A surgical cable system comprising:
a length of cable having a first end; and
a locking body for the length of cable in which the first cable end is operatively located,
the locking body defining a receiver for a first portion of the length of cable with the length of cable formed into a first loop that resides generally in a first plane; and
a locking structure on the locking body that cooperates with the first portion of the cable so as to maintain the first loop in a tensioned state,
the locking structure having a locked state and a released state,
the locking structure comprising an actuator that is operable to change the locking structure selectively from the released state into the locked state to thereby maintain the tensioned state of the first loop,
the locking structure changeable from the released state into the locked state as an incident of one of: a) moving at least a part of the actuator at least one of along and around an axis that is generally parallel to the first plane; and b); moving a part of the cable length along a first line that is generally parallel to the first plane,
wherein the locking structure comprises a wedging component that is separate from the locking body and configured to be moved by the actuator relative to the locking body to change the locking structure from the released state into the locked state,
wherein the wedging component is configured to urge a discrete length of the cable, that extends generally parallel to the axis, captively against a surface with the locking structure in the locked state,
wherein the actuator acts directly against each of the wedging component and the locking body,
wherein the actuator has a tapered configuration that acts between the wedging component and locking body to cause an increasing wedging force as the actuator is moved,
wherein the wedging component has a convex surface configured to engage the discrete length of the cable.

16. A surgical cable system comprising:
a length of cable having a first end; and a locking body for the length of cable in which the first cable end is operatively located, the locking body defining a receiver for a first portion of the length of cable with the length of cable formed into a first loop that resides generally in a first plane; and a locking structure on the locking body that cooperates with the first portion of the cable so as to maintain the first loop in a tensioned state, the locking structure having a locked state and a released state, the locking structure comprising an actuator that is operable to change the locking structure selectively from the released state into the locked state to thereby maintain the tensioned state of the first loop, the locking structure changeable from the released state into the locked state as an incident of one of: a) moving at least a part of the actuator at least one of along and around an axis that is generally parallel to the first plane; and b); moving a part of the cable length along a first line that is generally parallel to the first plane, wherein the locking structure comprises a wedging component that is configured to be moved by the actuator guidingly against and relative to the locking body to change the locking structure from the released state into the locked state, wherein the wedging component is configured to urge a discrete length of the cable, that extends generally parallel to the axis, captively against a surface with the locking structure in the locked state, wherein the actuator acts directly against each of the wedging component and the locking body, wherein the wedging component is moved from a first position spaced from the discrete length of the cable into a second position against the discrete length of the cable as an incident of which the locking structure is changed from the released state into the locked state.

17. The surgical cable system according to claim 16 further comprising biasing structure that acts against the wedging component, for urging the wedging component towards the first position.

18. A surgical cable system comprising:

a length of cable having a first end; and a locking body for the length of cable in which the first cable end is operatively located, the locking body defining a receiver for a first portion of the length of cable with the length of cable formed into a first loop that resides generally in a first plane; and a locking structure on the locking body that cooperates with the first portion of the cable so as to maintain the first loop in a tensioned state, the locking structure having a locked state and a released state, the locking structure comprising an actuator that is operable to change the locking structure selectively from the released state into the locked state to thereby maintain the tensioned state of the first loop, the locking structure changeable from the released state into the locked state as an incident of one of: a) moving at least a part of the actuator at least one of along and around an axis that is generally parallel to the first plane; and b); moving a part of the cable length along a first line that is generally parallel to the first plane, wherein the locking structure comprises a wedging component that is configured to be moved by the actuator relative to the locking body to change the locking structure from the released state into the locked state, wherein the actuator acts directly against the wedging component, wherein the wedging component is configured to urge a discrete length of the cable, that extends generally parallel to the axis, captively against a surface with the locking structure in the locked state, wherein with the locking structure in the locked state the wedging component urges one discrete length of the first portion of the length of cable against a second discrete length of the first portion of the length of cable and against the locking body.

19. A surgical cable system comprising:

a length of cable having a first end; and a locking body for the length of cable in which the first cable end is operatively located, the locking body defining a receiver for a first portion of the length of cable with the length of cable formed into a first loop that resides generally in a first plane; and a locking structure on the locking body that cooperates with the first portion of the cable so as to maintain the first loop in a tensioned state, the locking structure having a locked state and a released state, the locking structure comprising an actuator that is operable to change the locking structure selectively from the released state into the locked state to thereby maintain the tensioned state of the first loop, the locking structure changeable from the released state into the locked state as an incident of one of: a) moving at least a part of the actuator at least one of along and around an axis that is generally parallel to the first plane; and b); moving a part of the cable length along a first line that is generally parallel to the first plane, wherein the locking structure comprises a wedging component that is separate from the locking body and configured to be moved by the actuator relative to the locking body to change the locking structure from the released state into the locked state, wherein the actuator acts directly against the locking body, wherein the wedging component is configured to urge a discrete length of the cable, that extends generally parallel to the axis, captively against a surface with the locking structure in the locked state, wherein the locking structure is operable to change the locking structure from the locked state into the released state to thereby allow tension on the first loop to be reduced and the first loop to be reconfigured, wherein the wedging component is movable towards and away from the discrete length of the cable and the surface with the discrete length of the cable against the surface.

20. The surgical cable system according to claim 19 wherein the surgical cable system further comprises a biasing structure that urges the wedging component towards a first position in which the wedging component resides with the locking structure in the released state.

21. A surgical cable system comprising:

a length of cable having a first end; and a locking body for the length of cable in which the first cable end is operatively located, the locking body defining a receiver for a first portion of the length of cable with the length of cable formed into a first loop that resides generally in a first plane; and a locking structure on the locking body that cooperates with the first portion of the cable so as to maintain the first loop in a tensioned state, the locking structure having a locked state and a released state, the locking structure comprising an actuator that is operable to change the locking structure selectively from the released state into the locked state to thereby maintain the tensioned state of the first loop, the locking structure changeable from the released state into the locked state as an incident of one of: a) moving at least a part of the actuator at least one of along and around an axis that is generally parallel to the first plane; and b); moving a part of the cable length along a first line that is generally parallel to the first plane, wherein the locking structure comprises a wedging component that is separate from the locking body and configured to be moved by the actuator relative to the locking body to change the locking structure from the released state into the locked state, wherein the wedging component is configured to urge a discrete length of the cable, that extends generally parallel to the axis, captively against a surface with the locking structure in the locked state, wherein the actuator acts directly against each of the wedging component and the locking body, wherein the actuator has a tapered configuration that acts between the wedging component and locking body to cause an increasing wedging force as the actuator is moved wherein the wedging component has first and second ends spaced along the actuator axis and the wedging component pivots against and relative to the locking body about an axis at only the first end as the wedging component is moved to change the locking structure from the released state into the locked state.

* * * * *